United States Patent
Sullivan et al.

(10) Patent No.: US 9,938,223 B2
(45) Date of Patent: Apr. 10, 2018

(54) CATALYTIC TRANSESTERIFICATION OF ESTER COMPOUNDS WITH GROUPS REACTIVE UNDER TRANSESTERIFICATION CONDITIONS

(71) Applicant: SIRRUS, INC., Loveland, OH (US)

(72) Inventors: Jeffrey M. Sullivan, Goshen, OH (US); Aniruddha Palsule, Cincinnati, OH (US); Peter Rulon Stevenson, Loveland, OH (US); Kshitij Kishen Parab, Loveland, OH (US)

(73) Assignee: Sirrus, Inc., Loveland, OH (US)

( * ) Notice: Subject to any disclaimer, the term of this patent is extended or adjusted under 35 U.S.C. 154(b) by 0 days.

(21) Appl. No.: 15/099,831

(22) Filed: Apr. 15, 2016

(65) Prior Publication Data

US 2016/0229786 A1    Aug. 11, 2016

Related U.S. Application Data

(63) Continuation of application No. 14/814,961, filed on Jul. 31, 2015, now Pat. No. 9,416,091.

(60) Provisional application No. 62/111,919, filed on Feb. 4, 2015, provisional application No. 62/198,844, filed on Jul. 30, 2015.

(51) Int. Cl.
| *C07C 67/02* | (2006.01) |
| *C07C 67/03* | (2006.01) |
| *C07C 69/593* | (2006.01) |
| *C07C 69/604* | (2006.01) |
| *C07C 69/732* | (2006.01) |

(52) U.S. Cl.
CPC ............. *C07C 67/02* (2013.01); *C07C 67/03* (2013.01); *C07C 69/593* (2013.01); *C07C 2101/14* (2013.01); *C07C 2102/42* (2013.01)

(58) Field of Classification Search
CPC ....... C07C 67/02; C07C 67/03; C07C 69/593; C07C 69/604; C07C 69/732; C07C 2101/14; C07C 2102/42; C07C 2601/14; C07C 2602/42
See application file for complete search history.

(56) References Cited

U.S. PATENT DOCUMENTS

| 2,212,506 A | 8/1940 | Bachman |
| 2,245,567 A | 6/1941 | Brant et al. |
| 2,403,791 A | 7/1941 | D'Aiello |
| 2,277,479 A | 3/1942 | D'Aiello |
| 2,313,501 A | 3/1943 | Bachman |
| 2,330,033 A | 9/1943 | D'Aiello |
| 3,042,710 A | 7/1962 | Dickstein et al. |
| 3,197,318 A | 7/1965 | Halpern et al. |
| 3,203,915 A | 8/1965 | D'Alelio |
| 3,221,745 A | 12/1965 | Coover et al. |
| 3,427,250 A | 2/1969 | Haas et al. |
| 3,489,663 A | 1/1970 | Bayer et al. |
| 3,523,097 A | 8/1970 | Coover et al. |
| 3,557,185 A | 1/1971 | Ito et al. |
| 3,591,676 A | 7/1971 | Hawkins |
| 3,595,869 A | 7/1971 | Shuman |
| 3,677,989 A | 7/1972 | Jenkinson |
| 3,758,550 A | 9/1973 | Eck et al. |
| 3,923,836 A | 12/1975 | Bender |
| 3,936,486 A | 2/1976 | Egger et al. |
| 3,940,362 A | 2/1976 | Overhurlts |
| 3,945,891 A | 3/1976 | Aal et al. |
| 3,966,562 A | 6/1976 | Mukushi et al. |
| 3,975,422 A | 8/1976 | Buck |
| 3,978,422 A | 8/1976 | Rheinfelder |
| 3,995,489 A | 12/1976 | Smith et al. |
| 4,001,345 A | 1/1977 | Gorton et al. |
| 4,004,984 A | 1/1977 | Margen |
| 4,018,656 A | 4/1977 | Rogers et al. |
| 4,035,243 A | 7/1977 | Katz et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,080,238 A | 3/1978 | Wolinski et al. |
| 4,083,751 A | 4/1978 | Choi et al. |
| 4,102,809 A | 7/1978 | Smith et al. |
| 4,105,688 A | 8/1978 | Arni et al. |

(Continued)

FOREIGN PATENT DOCUMENTS

| CN | 102901754 A | 1/2013 |
| DE | 19508049 A1 | 9/1996 |
| EP | 2768917 A2 | 2/2009 |
| FR | 2788516 A1 | 7/2000 |

(Continued)

OTHER PUBLICATIONS

Eckert et al., "Prediction of acidity in acetonitrile solution with COSMO-RS," Journal of Computational Chemistry, 30(5), 2009, 799-810.*
Bachman et al., "Diethyl Methylenemalonate" Contirbution from the Research Laboratories of the Eastman Kodak Company, May 17, 1939, pp. 493-501.
"Knoevenagel reaction on a molecular sieve", Li Qifang et al., Chinese Science Bulletin, 1987, vol. 12, pp. 914-917.

(Continued)

*Primary Examiner* — Pancham Bakshi
*Assistant Examiner* — Mark R Luderer
(74) *Attorney, Agent, or Firm* — Young Basile Hanlon & MacFarlane, P.C.

(57) ABSTRACT

Disclosed are methods for the catalytic transesterification of compounds having one or more ester groups and groups reactive under transesterification conditions, such as 1,1-disubstituted alkene compounds, with alcohols or esters and novel compositions prepared therefrom. Further disclosed are novel compounds and compositions prepared as a result of the methods.

16 Claims, No Drawings

(56) References Cited

U.S. PATENT DOCUMENTS

| | | |
|---|---|---|
| 4,140,584 A | 2/1979 | Margen |
| 4,148,693 A | 4/1979 | Williamson |
| 4,154,914 A | 5/1979 | Kuraya |
| 4,160,864 A | 7/1979 | Ponticello et al. |
| 4,176,012 A | 11/1979 | Bryant |
| 4,186,058 A | 1/1980 | Katz et al. |
| 4,186,060 A | 1/1980 | Katz et al. |
| 4,198,334 A | 4/1980 | Rasberger |
| 4,224,112 A | 9/1980 | Childs |
| 4,229,263 A | 10/1980 | Childs |
| 4,236,975 A | 12/1980 | Childs |
| 4,237,297 A | 12/1980 | Rody et al. |
| 4,243,493 A | 1/1981 | Gruber et al. |
| 4,256,908 A | 3/1981 | Nishimura et al. |
| 4,282,067 A | 8/1981 | Katz et al. |
| 4,282,071 A | 8/1981 | Sherrod |
| 4,291,171 A | 9/1981 | Baum et al. |
| 4,313,865 A | 2/1982 | Teramoto et al. |
| 4,319,964 A | 3/1982 | Katz et al. |
| 4,329,479 A | 5/1982 | Yabutani et al. |
| 4,396,039 A | 8/1983 | Klenk et al. |
| 4,399,300 A | 8/1983 | Prange et al. |
| 4,411,740 A | 10/1983 | Flanigam et al. |
| 4,440,601 A | 4/1984 | Katz et al. |
| 4,440,910 A | 4/1984 | O'Connor |
| 4,443,624 A | 4/1984 | Prange et al. |
| 4,444,928 A | 4/1984 | Karrer |
| 4,450,067 A | 5/1984 | Angevine et al. |
| 4,503,074 A * | 3/1985 | Friedman ............... C07C 69/708 514/547 |
| 4,504,658 A | 3/1985 | Narisada et al. |
| 4,510,273 A | 4/1985 | Miura et al. |
| 4,517,105 A | 5/1985 | Laemmle et al. |
| 4,539,423 A | 9/1985 | Itatani et al. |
| 4,556,649 A | 12/1985 | Salzburg et al. |
| 4,560,723 A | 12/1985 | Millet et al. |
| 4,578,503 A | 3/1986 | Ishikawa et al. |
| 4,584,064 A | 4/1986 | Ciais et al. |
| 4,613,658 A | 9/1986 | Mathias et al. |
| 4,698,333 A | 10/1987 | Fauss et al. |
| 4,720,543 A | 1/1988 | McPherson et al. |
| 4,727,701 A | 3/1988 | Figari |
| 4,728,701 A | 3/1988 | Jarvis et al. |
| 4,736,056 A | 4/1988 | Smith et al. |
| 4,767,503 A | 8/1988 | Crescentini et al. |
| 4,769,464 A | 9/1988 | Sajtos |
| 4,783,242 A | 11/1988 | Robbins |
| 4,835,153 A | 5/1989 | Kabota et al. |
| 4,897,473 A | 1/1990 | Dombek |
| 4,914,226 A | 4/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |
| 5,064,507 A | 11/1991 | O'Donnell |
| 5,142,098 A | 8/1992 | Bru-Magniez et al. |
| 5,162,545 A | 11/1992 | Etzbach et al. |
| 5,210,222 A | 5/1993 | O'Murchu |
| 5,227,027 A | 7/1993 | Topper |
| 5,259,835 A | 11/1993 | Clark et al. |
| 5,284,987 A | 2/1994 | Sikkenga et al. |
| 5,292,937 A | 3/1994 | Manning et al. |
| 5,328,687 A | 4/1994 | Leung et al. |
| 5,312,864 A | 5/1994 | Wenz et al. |
| 5,334,747 A | 8/1994 | Steffen |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,565,525 A | 10/1996 | Morimoto et al. |
| 5,567,761 A | 11/1996 | Song |
| 5,575,997 A | 11/1996 | Leung et al. |
| 5,582,834 A | 12/1996 | Leung et al. |
| 5,614,650 A | 3/1997 | Sandler et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,054,606 A | 4/2000 | Irie et al. |
| 6,069,261 A | 5/2000 | Hoffmann et al. |
| 6,106,807 A | 8/2000 | Albayrak et al. |
| 6,143,352 A | 11/2000 | Clark et al. |
| 6,183,593 B1 | 2/2001 | Narang et al. |
| 6,210,474 B1 | 4/2001 | Romano, Jr. et al. |
| 6,211,273 B1 | 4/2001 | Bru-Magniez et al. |
| 6,238,896 B1 | 5/2001 | Ozaki et al. |
| 6,255,038 B1 | 5/2001 | Smith et al. |
| 6,245,933 B1 | 6/2001 | Malofsky et al. |
| 6,284,915 B2 | 9/2001 | Hirase et al. |
| 6,291,703 B1 | 9/2001 | Schaerfl et al. |
| 6,376,019 B1 | 4/2002 | Leung |
| 6,395,737 B1 | 5/2002 | Defossa et al. |
| 6,395,931 B1 | 5/2002 | Carvalho et al. |
| 6,413,415 B1 | 7/2002 | Weiss et al. |
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,518,677 B1 | 2/2003 | Capote |
| 6,545,097 B2 | 4/2003 | Pinchuk et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,716,355 B1 | 4/2004 | Hanemaaijer et al. |
| 6,750,298 B1 | 6/2004 | Bru-Magniez et al. |
| 6,794,365 B2 | 9/2004 | Al-Obeidi et al. |
| 6,841,064 B1 | 1/2005 | Weiss et al. |
| 6,936,140 B2 | 8/2005 | Paxton et al. |
| 7,070,675 B2 | 7/2006 | Schmidt et al. |
| 7,109,369 B2 | 9/2006 | Nose et al. |
| 7,208,621 B2 | 4/2007 | Nose et al. |
| 7,226,957 B1 | 6/2007 | Scranton et al. |
| 7,305,850 B2 | 12/2007 | Tonkovich et al. |
| 7,553,989 B2 | 6/2009 | Sawabe et al. |
| 7,603,889 B2 | 10/2009 | Cypes et al. |
| 7,610,775 B2 | 11/2009 | Tonkovich et al. |
| 7,649,108 B2 | 1/2010 | Schal et al. |
| 7,659,423 B1 | 2/2010 | McArdle |
| 7,663,000 B2 | 2/2010 | Dekkers et al. |
| 7,771,567 B2 | 8/2010 | Rives et al. |
| 7,829,738 B1 | 11/2010 | Brammer et al. |
| 7,900,558 B2 | 3/2011 | Yokoi |
| 8,425,999 B2 | 4/2013 | McArdle et al. |
| 8,609,885 B2 | 12/2013 | Malofsky et al. |
| 8,884,051 B2 | 11/2014 | Malofsky et al. |
| 9,108,914 B1 | 8/2015 | Malofsky et al. |
| 9,181,365 B2 | 11/2015 | Malofsky et al. |
| 9,217,098 B1 | 12/2015 | Malofsky et al. |
| 9,221,739 B2 | 12/2015 | Malofsky et al. |
| 9,234,107 B2 | 1/2016 | Malofsky et al. |
| 9,334,430 B1 | 5/2016 | Stevenson et al. |
| 9,416,091 B1 * | 8/2016 | Sullivan ................. C07C 67/02 |
| 9,481,640 B2 | 11/2016 | McArdle et al. |
| 2001/0005572 A1 | 6/2001 | Lobo et al. |
| 2001/0034300 A1 | 10/2001 | Yurugu et al. |
| 2002/0035231 A1 * | 3/2002 | Whitehouse ........... C08G 18/34 528/44 |
| 2002/0143128 A1 | 10/2002 | Cabioch et al. |
| 2002/0151629 A1 | 10/2002 | Buffkin et al. |
| 2003/0096069 A1 | 5/2003 | D'Alessio |
| 2003/0199655 A1 | 10/2003 | Yurugi et al. |
| 2004/0076601 A1 | 4/2004 | Bru-Magniez et al. |
| 2004/0082043 A1 | 4/2004 | Yadav |
| 2004/0220060 A1 | 11/2004 | Bartley et al. |
| 2006/0167267 A1 | 7/2006 | Chorghade et al. |
| 2006/0211809 A1 | 9/2006 | Kodemura et al. |
| 2007/0043145 A1 | 2/2007 | Beck et al. |
| 2007/0049655 A1 | 3/2007 | Yoshimune et al. |
| 2007/0092483 A1 | 4/2007 | Pollock |

(56) References Cited

U.S. PATENT DOCUMENTS

| | | |
|---|---|---|
| 2007/0120630 A1 | 10/2007 | Malofsky et al. |
| 2007/0238872 A1 | 10/2007 | Sabesan |
| 2008/0131618 A1 | 6/2008 | Nakamura et al. |
| 2008/0160305 A1 | 7/2008 | Warren et al. |
| 2008/0187655 A1 | 8/2008 | Markle et al. |
| 2008/0227919 A9 | 9/2008 | Li et al. |
| 2008/0241485 A1 | 10/2008 | Shimomura et al. |
| 2008/0286333 A1 | 11/2008 | Kangas et al. |
| 2009/0203861 A1 | 8/2009 | Lee et al. |
| 2009/0206861 A1 | 8/2009 | Lee et al. |
| 2009/0263604 A1 | 10/2009 | Arai et al. |
| 2010/0016508 A1 | 1/2010 | Sasagawa et al. |
| 2010/0256720 A1 | 10/2010 | Overstreet et al. |
| 2010/0286433 A1 | 11/2010 | Malofsky et al. |
| 2010/0286438 A1 | 11/2010 | Malofsky et al. |
| 2011/0015406 A1 | 1/2011 | Umentani et al. |
| 2011/0024392 A1 | 2/2011 | Sato et al. |
| 2011/0164322 A1 | 7/2011 | Morozumi et al. |
| 2011/0245522 A1* | 10/2011 | Wu .................. C11C 3/003 554/161 |
| 2012/0083523 A1 | 4/2012 | Richard et al. |
| 2012/0136130 A1 | 5/2012 | Takashima et al. |
| 2012/0203021 A1 | 8/2012 | Friese et al. |
| 2013/0019520 A1 | 1/2013 | Sello et al. |
| 2013/0281580 A1 | 10/2013 | Malofsky et al. |
| 2013/0303719 A1 | 11/2013 | Malofsky et al. |
| 2013/0324754 A1 | 12/2013 | Bredsguard |
| 2014/0058031 A1 | 2/2014 | Overbeek et al. |
| 2014/0248485 A1 | 9/2014 | Malofsky et al. |
| 2014/0275400 A1 | 9/2014 | Chen et al. |
| 2014/0288230 A1 | 9/2014 | Malofsky et al. |
| 2014/0329980 A1 | 11/2014 | Malofsky et al. |
| 2015/0056879 A1 | 2/2015 | Malofsky et al. |
| 2015/0073110 A1 | 3/2015 | Malofsky et al. |
| 2015/0104660 A1 | 4/2015 | Malofsky et al. |
| 2015/0148480 A1 | 5/2015 | Ellison et al. |
| 2015/0210894 A1 | 7/2015 | Malofsky et al. |
| 2015/0303122 A1 | 10/2015 | Malofsky et al. |
| 2015/0361283 A1 | 12/2015 | Malofsky et al. |

FOREIGN PATENT DOCUMENTS

| | | |
|---|---|---|
| GB | 432628 A | 7/1935 |
| GB | 965676 | 8/1964 |
| GB | 965767 | 8/1964 |
| GB | 975733 | 11/1964 |
| JP | H02281013 | 11/1990 |
| JP | H08231564 | 9/1996 |
| JP | 09258448 A | 10/1997 |
| JP | 200019936 | 7/2000 |
| JP | 2003201397 A | 7/2003 |
| JP | 2008/174494 | 1/2007 |
| WO | 1999/046619 | 9/1999 |
| WO | 1999/055394 A1 | 11/1999 |
| WO | 2007/120630 A2 | 10/2007 |
| WO | 2010/091975 A1 | 8/2010 |
| WO | 2010/129068 A1 | 11/2010 |
| WO | 2011/059104 A1 | 5/2011 |
| WO | 2011/161045 A1 | 12/2011 |
| WO | 2012/054616 A2 | 4/2012 |
| WO | 2012/054633 A2 | 4/2012 |
| WO | 2013/059473 A2 | 4/2013 |
| WO | 2013/066629 | 5/2013 |
| WO | 2013/149165 A1 | 10/2013 |
| WO | 2013/149168 A1 | 10/2013 |
| WO | 2013/149173 A1 | 10/2013 |
| WO | WO2013149165 | * 10/2013 |

OTHER PUBLICATIONS

"Knoevenagel Condensation Over Acidic Zeolite", Zuo Bojun et al., Chinese Journal of Catalysis, Nov. 2002, vol. 23 (6), pp. 555-558.

"Comparison of the catalytic activity of MOFs and zeolites in Knoevenagel condensation", Maksym Opanasenko, et al., Catalysis Science & Technology, 2013, vol. 3 pp. 500-507.

Corey et al. "Total Synthesis of Gibberellic Acid. A Simple Synthesiss of a Key Intermediate", J. Am. Chem. Soc. 1982, 104, pp. 6129-6130.

Krishna et al. "Stereodefined Access to 3-Deoxy Sugars Through a Tandem Baylis-Hillman and Lewis Acid Catalyzed Sequence", European Journal of Organic Chemistry, 2010, pp. 813-817.

March, Advanced Organic Chemistry, 2d Ed, section 0-25 pp. 365-367, 1977 McGraw Hill, New York, New York.

Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.

McNab, Kirk-Othmer Encyclopedia of chemical Technology, Pyrolysis, Flash Vacuum, 2009, John Wiley & Sons, Inc., pp. 1-26.

Block, "Diethyl bis (hydroxymethyl) malonate" Organic Syntheses, 1973, Coll. vol. 5, p. 381 [vol. 40, p. 27 (1960); Retrieved on Apr. 4, 2014 from internet: http://www.Orgsyn.org/content/pdfs/procedures/cv5p0381.pdf] p. 381, para 1.

Reddy et al. "An easy-to-use heterogeneous promoted zirconia catalyst for Knoevenagel condensation in liquid phase under solvent-free conditions." Journal of Molecular Catalysts A: Chemical 258 (2006) pp. 302-307.

M. Ware et al.: "DBU: An Efficient Catalyst for Knoeveganel Condensation under Solvent-free Condition," Bulletin of the Catalysis Society of India, (2007), vol. 6, pp. 104-106.

V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.

J. S. Yadav et al.,: "Phosphane-Catalyzed Knoevenagel Condensation: a Facile Synthesis of a-Cyanoacrylates and a-Cyanoacrylonitriles," Eur, J, Org, Chem. (2004), pp. 546-551.

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org <http://Euro.J.Org>. Chem., (2006), pp. 3767-3770.

H, A, Oskooie et al.: "On Water: an Efficient Knoevenagel Condensation using 12-Tungstophosphoric Acid as a Reusable Green Catalyst," Synthetic Communications, (2006), vol. 36, pp. 2819-2823.

H. Jiang et al.: "Inorganic Zinc Salts Catalyzed Knoevenagel Condensation at Room Temperature without Solvent," Preparative Biochemistry & Biotechnology, (2009), vol. 39, pp. 194-200.

T. Doi et al.: "Synthesis of Dimethyl gloiosiphne A by Way of Palladium-Catalyzed Domino Cyclization," T. Ora <htto://T.Ora>. Chem., (2007), vol. 72, pp. 3667-3671.

H. Jung et al,: "New and General Methods for the Synthesis of Arylmethylene Bis(3-Hydroxy-2-Cyclohexene-1-Ones) and Xanthenediones by EDDA and In(OTf)3-Catalyzed One-Pot Domino Knoevenagei/Michael or Koevenagei/Michaei/Cyclodehydration Reactions," Bull. Korean Chem. Soc. (2009) vol. 30, No. 9, pp. 1989-1995.

P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.

P. Klemarwczyk: "A General Synthesis of 1,1 Disubstituted Electron Deficient Olefins and their Polymer Properties," Polymer,— (1998), vol. 39, No. I, pp. 173-181.

Gill, Charansingh, et al. "Knoevenagel condensation in neutral media: A simple and efficient protocol for the synthesis of electrophillic alkenes catalyzed by anhydrous ferric sulphate with remarkable reusability." Bulletin of the Catalysis Society of India 7 (2008): 153-157.

P, Ballesteros et al.: "D 1-tert-Butyl Methylenemalonate [Propanedioic Acid, Methylene-, bis( 1,1-dimethylethyl)ester]," Organic Syntheses. coli. (1990), vol. 7, p. 142; (1986) vol. 64, p. 63.

A. M. Vetrova et al.: "Improvement of the Thermal Stability of Cyanoacrylate Adhesives," Polymer Science, Series D, (2009), vol. 2, No. 1, pp. 27-30.

(56) References Cited

OTHER PUBLICATIONS

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.
G. Lai et al.: "Ionic Liquid Functionalized Silica Gel: Novel Catalyst and Fixed Solvent," Tetrahedron Letters (2006), vol. 47, pp. 6951-6953.
J. R. Harjani et al.: "Lewis Acidic Ionic Liquids for the Synthesis of Electrophilic Alkenes; via the Knoevenagel Condensation," Tetrahedron Letters, (2002), vol. 43, pp. 1127-1130.
P. Ballesteros et al.: "Synthesis of DI-tent-Butyl Methylenemalonate, a Sterically Hindered 1,1-Dicarbonyl Alkene," J. Ora <htto://J.Ora>. Chem, (1983), vol. 48, pp. 3603-3605.
M. Matziari et al. Active Methylene Phosphinic Peptides: A new Diversification Approach Organic Letters 2006 vol. 8, No. 11 pp. 2317-2319 May 5, 2006.
Zaragoza Dorwald, Side Reactions in Organic Synthesis, 2005, Wiley-VCH Verlag GmbH & Co., KgaA, Weinheim, Preface. p. IX.
K. Okamura and T. Date, A Facile Conversion of Ethoxydihydropyrans to 4-Cyanoethylisoxazoles, J. Heterocyclic Chem. 33, 383 (1996).
NPL Yamauchi et al. Tetrahedron Asymetry 12, (2001), 3113-3118.
Cristoph Schotes et al. "Cu(I)- and C(II)-Catalyzed Cyclo- and Michael Addition Reactions of Unsaturated [beta]-Ketoesters" The Journal of Organic Chemistry, vol. 76, No. 14 dated Jul. 15, 2011 p. 5862-5866.
Alejandro Bugarin et al. "Efficient direct [alpha]-methylenation of carbonyls mediated by dissopropylammonium trifluoroacetate", Chemical Communications, vol. 46, No. 10 dated Jan. 25, 2010.
H. Hoffman et al. "Preparation and Selected Reaction of tery-Butyl 2-Methylene-3-oxoalkanoates" Chem. Ber., vol. 124 dated Jan. 1, 1991, pp. 2475-2480.
M. Yamauchi et al. "Reactivity of 2-Methylene-1, 3-dicarbonyl Compounds. 1,3-Dipolar Cycloaddition Reaction with Ethyl Diazoacetate", Chem. Pham. Bull., vol. 49, No. 12, dated Jan. 1, 2001, pp. 1638-1639.
Lawrence N J et al. "Reaction of Baylis-Hillman products with Swern and Dess-Martin oxidants", Tetrahedron Letters, Pergamon, GB, vol. 42 No. 23 dated Jun. 4, 2001, pp. 3939-3941.
Juliana Vale et al. "Efficient [alpha]-Methylenation of Carbonyl Compounds in Ionic Liquids at Room Temperature", SYNLETT, vol. 2009, No. 01, Jan. 1, 2009 (Jan. 1, 2009), pp. 75-78, XP055170349, ISSN: 0936-5214, DOI: 10.1055/s-0028-1087389 *table 2; compound 3 *.
P. Breton et al., "New Poly(Methylidudene Malonate 2.1.2) Nanoparticles: Recent Developments", Targeting of Drugs 4, NATO ASI Series, vol. 273, pp. 161-172, 1994.
Limouzin et al., "Anionic Polymerization of n-Butyl Cyanoacrylate in Emulsion and Miniemulsion" Macromolecules, vol. 36, 2003, pp. 667-674.
Morrison and Boyd, *Organic Chemistry*, $4_{th}$ Ed, pp. 831 and 836-838, 1983 Allyn Bacon, Inc. Boston, Massachusetts.
Otera et al, "Esterification: Methods, Reactions, & Applications" "Esterification of Sludge Palm Oil Using Trifluromethanesulfonic Acid for preparation of Biodiesel Fuel" Korean Journal of Chemical Engineering, Jun. 2013, vol. 30, Issue 6, pp. 1229-1234.
Thimmaraju et al.,"Transsesterification of diethyl malonate with Benzyl Alcohol Catalyzed by Modified Zirconia: Kinetic Study", Journal of Molecular Catalysis A: Chemical, vol. 391, Sep. 2014, pp. 55-65.
Olah et al, "Superelectrophilic Solvation," Accounts of Chemical Research, Apr. 2004, vol. 37, No. 4.
Kütt et al, "Equilibrium Acidities of Superacids," Journal of Organic Chemistry, vol. 76, No. 2, 2011, pp. 391-395, published on the web Dec. 17, 2010.
McCoy, M. "A New Way to Stick" Chemical & Engineering News, vol. 92, Issue 26, Jun. 30, 2014, pp. 17-18, paragraph [2].

\* cited by examiner

CATALYTIC TRANSESTERIFICATION OF ESTER COMPOUNDS WITH GROUPS REACTIVE UNDER TRANSESTERIFICATION CONDITIONS

FIELD

Disclosed are methods for the catalytic transesterification of compounds having one or more ester groups and groups reactive under transesterification conditions, such as 1,1-disubstituted alkene compounds, with alcohols or esters and novel compositions prepared therefrom. Further disclosed are novel compounds and compositions prepared as a result of the methods.

BACKGROUND

Transesterification is a process whereby an ester group's functionality is modified by exchanging groups with a suitable reagent (such as an alcohol). This process is well-known as disclosed in March, *Advanced Organic Chemistry*, 2d Ed, section 0-25 pp 365-7, 1977 McGraw Hill, New York, N.Y.; and Morrison and Boyd, Organic Chemistry, 4$^{th}$ Ed, pp 831 and 836-8, 1983 Allyn Bacon, Inc. Boston, Mass. The process may often require high temperatures, such as 150° C. or above, and a relatively high amount of the catalyst(s). Many transesterification reactions are base catalyzed, which is accomplished by assisting in the removal a proton from the reagent (such as an alcohol) making it more nucleophilic to undergo transesterification. Transesterification is easily identified as an equilibrium process benefiting from the removal of byproducts to achieve higher yields of the desired product(s). These exemplary characteristics of the process can often limit its commercial utilization—especially in relation to the various reactants and/or reagents utilized where the stability of the reaction can be compromised.

Transesterification of highly reactive unsaturated esters, such as 1,1-disubstituted alkene compounds which have one or more ester groups as substituents, can be problematic under some well-known transesterification conditions. 1,1-Disubstituted alkene compounds readily undergo anionic polymerization in the presence of weak bases and nucleophiles under ambient conditions, as well as free radical initiated polymerization and auto-polymerization upon exposure to elevated temperatures for prolonged periods of time. The transesterification of these types of reactive species precludes employing base catalyzed transesterification and the use of basic and/or nucleophilic catalysts. Malofsky et al. WO 2013/059473, incorporated herein by reference in its entirety for all purposes, discloses the preparation of multifunctional methylene malonates by multiple synthetic schemes. One disclosed process involves reacting a methylene malonate with a polyol in the presence of a catalyst to prepare compounds wherein one of the ester groups on the methylene malonates undergoes transesterification to react with the polyol and form multifunctional compounds (multifunctional meaning the presence of more than one methylene malonate core unit).

The compounds formed via transesterification have two or more methylene malonate moieties bonded to the oxygen atoms on the polyol. Additionally, the use of enzyme catalysis is disclosed. Enzymatic catalysts work well but can be expensive and recyclability attempts often result in drastically deficient or no observable catalytic activity for these transesterification reactions. The use of expensive catalysts and lack of recyclability can restrict scale-up opportunities concerning these monomers. The alternative process for preparing various ester and diester 1,1-disubstituted alkene compounds is to first form the precursor 1,1-diester alkylate compounds (i.e., the non-reactive or anionically polymerizable compounds). This is a multistep process and complex separation processes may be required depending on the monomers synthesized (see Malofsky et al., U.S. Pat. Nos. 8,609,885 and 8,884,051). Additionally, each 1,1-disubstituted alkene compound requires different catalytic cracking and product separation conditions. This suggests that multiple reactors and isolated separation hardware modules are required for each individual compound. Ultimately, under these described processing conditions, the capital and change over costs for manufacturing different 1,1-disubstituted alkene compounds in viable commercial quantities would be quite high.

Ester containing compounds that contain reactive functional groups (such as 1,1-disubstituted alkenes) can undergo undesired side reactions under typical transesterification reaction conditions. Exemplary side reactions include polymerization through the reactive alkene functionality via free radical and/or anionic mechanisms, Michael addition of reagent alcohol to the alkene functional group, Michael addition of the reaction byproduct alcohol with the alkene functionality, and the like. Exemplary classes of compounds that can undergo such side reactions include 1,1-disubstituted alkenes (such as methylene malonates) wherein the substituents are electron withdrawing, cyanoacrylates, acrylates, methacrylates, and the like. The possibility of such side reactions can limit the use of transesterification for such reactive compounds. Furthermore, the implementation of base catalysts for transesterification of such reactive systems is not possible, as the nucleophilic nature of the catalyst would anionically initiate polymerization—a competing reaction to transesterification if that were to occur.

Thus, a method for transesterifying ester containing reactive compounds (including 1,1-disubstituted alkene compounds) is needed which utilizes a cost efficient and compatible catalyst system. Additionally, a process that efficiently transesterifies compounds that may alternatively undergo undesired side reactions via typical transesterification conditions is needed. Also needed is an improved, more defined synthetic or manufacturing process for preparing multiple 1,1-disubstituted alkene compounds with varied ester substituent groups or monomer functionality.

SUMMARY

Disclosed are methods comprising: contacting a first ester compound having one or more ester groups with hydrocarbyl moieties as part of each of the ester groups and a functional group which may undergo undesired side reactions under transesterification reaction conditions, with one or more alcohols having a hydrocarbon backbone and one or more hydroxyl groups or one or more second ester compounds having one or more ester groups with hydrocarbyl moieties different from the hydrocarbyl moieties on the first ester compounds, in the presence of one or more acids having a pKa in a polar aprotic solvent (i.e., acetonitrile) of about −5 to about 14 or esters of the acid under conditions that at least one of the hydrocarbyl moieties on the first ester compound is replaced by the alcohol hydrocarbon backbone or hydrocarbyl moieties from the second ester compounds. The hydrocarbon moieties removed from the first ester compound forms a second alcohol or a third ester compound wherein the second alcohol or third ester compound formed is a byproduct of the reaction and is removed. In some embodiments, the alcohols comprise a mixture of alcohols or the second ester compounds comprise a mixture of ester compounds. In some embodiments, the mixture of alcohols comprise at least one alcohol having one hydroxyl group and at least one alcohol having more than one hydroxyl group or the mixture of second ester compounds comprise at least one ester compound having one ester group and at least one ester compound having more than one ester group. In the embodiment wherein the second ester compound has two or more ester groups a hydrocarbon backbone may bond to the two or more ester groups through oxygen atoms. The acid or the ester of an acid is present in a sufficient amount to catalyze the replacement of one or more hydrocarbon moieties of the first ester compound with the hydrocarbon backbone of the one or more alcohols or a hydrocarbyl moiety from the one or more second compounds having one or more ester groups. In some embodiments, the one or more second compounds having one or more ester groups is an acetate ester or a formate ester.

The first ester compound may be a compound having another functional group which may react to form undesired byproducts under transesterification reaction conditions. The first ester compound may contain an unsaturated group. In some embodiments the first ester compounds is an α,β-unsaturated monoester, α,β-unsaturated 1,1-diester or α,β-unsaturated-1-cyano-1-ester. In some embodiments the first ester compound may contain an unsaturated compound which is located sufficiently near to an electron withdrawing group such that the unsaturated group exhibits enhanced reactivity, for instance will react with other compounds or polymerize more easily.

Disclosed are methods comprising: contacting a 1,1-disubstituted alkene compound with one or more alcohols having a hydrocarbon backbone and one or more hydroxyl groups or one or more second ester compounds with hydrocarbyl moieties different from the hydrocarbyl moieties on the 1,1-disubstituted alkene compounds, in the presence of one or more acids having a pKa in a polar aprotic solvent of about −5 to about 14 (for example superacids or esters of the acids) under conditions that one or both of the hydrocarbyl moieties on the first ester compound are replaced by the alcohol hydrocarbon backbone or a hydrocarbyl moieties from the one or more second ester compounds. The method allows for cost efficient preparation of: a wide variety of 1,1-disubstituted alkene compounds including diesters with different ester substituent groups (often referred to as asymmetric diesters), compounds with two or more core units of 1,1-disubstituted alkene compounds (often referred to as multifunctional compounds and mixtures of 1,1-disubstituted alkene compounds), and one or more multifunctional 1,1-disubstituted alkene compounds. The process of the invention allows for the synthesis of such mixtures to occur in one reactor vessel. In some embodiments the mixtures can be formed simultaneously. The acid or ester thereof, such as the super acid or ester thereof, is present in a sufficient amount to catalyze the replacement of one or more hydrocarbon moieties on the first ester compounds (such as 1,1-disubstituted alkene compounds). In some embodiments, the acid or ester thereof, super acid or ester thereof, may be present in an amount of about 0.1 molar equivalents or less, and in some embodiments about 0.01 molar equivalents or less based on the equivalents of the first ester compounds present (such as 1,1-disubstituted alkene compounds). In some embodiments it is desirable to remove the second alcohol or third ester compound byproduct formed from the leaving hydrocarbon moiety during the process.

Disclosed is a method as described previously, wherein excess molar equivalents of 1,1-disubstituted alkene compounds are contacted with one or more alcohols having two or more hydroxyl groups or second ester group containing compounds having two or more ester groups, to form compounds comprising two or more 1,1-disubstituted alkene compounds bonded directly to the alcohol hydrocarbon backbone or a hydrocarbon backbone disposed between two of the ester groups and bonded to the oxygen atom of the hydrocarbon backbone.

The method disclosed provides a cost effective method of replacing one or more of the hydrocarbon moieties on the ester groups of compounds such as 1,1-disubstituted alkene compounds and the preparation of multifunctional 1,1-disubstituted alkene compounds. The method facilitates the utilization of a processing plant which manufactures core 1,1-disubstituted alkene compounds in bulk and then facilitates subsequent transesterification of the core 1,1-disubstituted alkene compounds to prepare a variety of alternative compounds and mixtures of compounds with varied ester or diester substituents. The method allows for the manufacture of such mixtures in the same reactor and under certain conditions simultaneously.

DETAILED DESCRIPTION

The explanations and illustrations presented herein are intended to acquaint others skilled in the art with the invention, its principles, and its practical application. The specific embodiments of the present invention as set forth are not intended to be exhaustive or limiting of the invention. The scope of the invention should be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Unless defined otherwise, all technical and scientific terms used herein have the meaning commonly understood by a person skilled in the art to which this disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Disclosed is a process for transesterifying a compound having one or more ester groups and a functional group which may undergo undesired side reactions under typical transesterification reaction conditions to replace the hydrocarbyl moiety on the ester group of the compound with a different hydrocarbyl moiety. The transesterification is performed by contacting the first ester compound with one or more alcohols or one or more second ester compounds wherein the hydrocarbon backbones of the one or more alcohol compounds or one or more of the hydrocarbyl moieties of the second ester compounds replace the one or more of the hydrocarbyl moieties on one or more ester groups of the first ester compounds. The process can be performed at comparatively mild temperatures, such as 130° C. or less, with the aid of a catalyst at comparatively lower reaction loadings. Generally this process is illustrated by Equation 1 where an alcohol reagent is used to illustrate the transesterification reaction:

EQ1

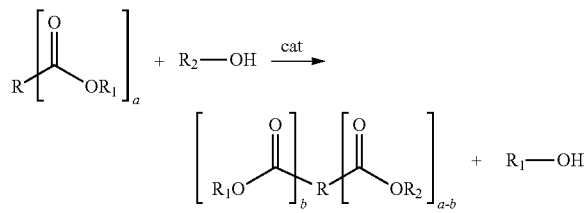

wherein R is, separately in each occurrence, a hydrocarbyl group substituted with a functional group which may undergo undesired side reactions under transesterification reaction conditions. $R_1$ and $R_2$ are, separately in each occurrence, hydrocarbyl groups. a is an integer of 1 or more and b is an integer of 0 or more, wherein b is equal to or less than a. This process is generally illustrated by Equation 2 where a second ester compound reagent is used to perform the transesterification:

EQ2

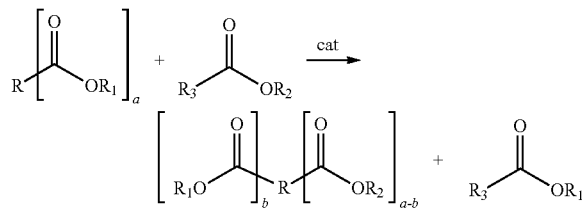

wherein R, $R_1$, $R_2$, a, and b are as described hereinbefore and $R_3$ is a hydrocarbyl group. The product produced is based on the starting reactants, conditions, and ratios of reactants.

Ester compounds refer to any compound containing one or more ester groups. The first ester compounds, which can be subject to ester group exchange or transesterification, are any compounds with one or more ester groups wherein hydrocarbyl moieties on the ester groups can leave and be replaced with other hydrocarbyl moieties and which contain a functional group which may undergo undesired side reactions under transesterification reaction conditions. Preferably the first ester compounds correspond to the formula:

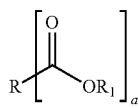

wherein R, $R_1$, and a are previously defined. As used herein, the first ester compound is an ester of the 1,1-disubstituted alkene compound which is subjected to the transesterification process and which is then altered by the process to form a desired product which can further be used as modified or can be used to synthesize other compounds or compositions. As used herein the second ester compound refers to a reagent ester that is present to provide a replacement hydrocarbyl moiety for the hydrocarbyl moiety leaving the first ester compound. In essence the first and second ester compounds alter reaction will have different hydrocarbyl moieties on the ester groups. Third ester compound is a byproduct formed from the second ester compound and a hydrocarbyl moiety leaving the first ester compound.

1,1-Disubstituted alkene compounds refer to compounds having one or more ester containing, electron withdrawing substituents including 1,1-diester alkenes, 1,1-disubstituted-1-alkenes, 1,1-diestersubstituted-1-alkenes, 1,1-diestersubstituted-1-alkylenes, methylene malonates, and methylene β-ketoesters. 1,1-Disubstituted alkene compounds refer to compounds having a carbon with a double bond attached thereto and which is further bonded to at least one carbonyl carbon atom of an ester as shown in Formula 1:

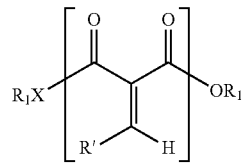

Formula 1 wherein R' is preferably hydrogen (illustrating the reactive alkene functionality) and X is another oxygen of an ester group (providing two substituent ester groups) or direct bond (such as a methylene β-ketoester). In some embodiments, R' may correspond to an alkyl or alkylene group thereby potentially rearranging the reactive center of the compound (as illustrated in Formula 1); nevertheless, these alternative compounds are herein referred to as 1,1-disubstituted alkene compounds. The 1,1-disubstituted alkene compounds can be prepared as disclosed in Malofsky et al., U.S. Pat. Nos. 8,609,885 and 8,884,051; and Malofsky et al. WO 2013/059473. The methylene beta-keto esters can be prepared as disclosed in Malofsky et al. US Publication 2014/0288230 incorporated herein by reference in its entirety for all purposes.

The term "monofunctional" refers to the first ester compounds (such as 1,1-disubstituted alkene compounds) having only one core unit. The core unit is represented within the brackets in Formula 1 depicting the associated reactive alkene functionality. The term "difunctional" refers to the first ester compounds or the desired ester product of the reaction, (such as 1,1-disubstituted alkenes compounds) having two core formulas (such as reactive alkene functionality) bound through a hydrocarbylene linkage between one oxygen atom on each of two core formulas. The term "multifunctional" refers to the first ester compounds or the desired ester product of the reaction (such as 1,1-disubstituted alkene compounds) having more than one core unit (such as reactive alkene functionality) which forms a chain through a hydrocarbylene linkage between one oxygen atom on each of two adjacent core formulas.

Acid catalyst, as used herein, is an acidic species that catalyzes the transesterification reaction while minimizing or not contributing to side reactions. The term alcohol hydrocarbon backbone refers to a backbone having carbon and hydrogen atoms, and may contain other heteroatoms, to which the hydroxyl of an alcohol is bonded. The term second ester hydrocarbon backbone refers to a backbone having carbon and hydrogen atoms, and may contain other heteroatoms, to which an ester compound is bonded (such as an acetate or a formate).

One or more as used herein means that at least one, or more than one, of the recited components may be used as disclosed. Nominal as used with respect to functionality refers to the theoretical functionality—generally this can be calculated from the stoichiometry of the ingredients used. Heteroatom refer to atoms that are not carbon or hydrogen such as nitrogen, oxygen, sulfur, and phosphorus; more preferred heteroatoms include nitrogen and oxygen. Hydrocarbyl, as used herein, refers to a group containing one or more carbon atom backbones and hydrogen atoms, which may optionally contain one or more heteroatoms. Where the hydrocarbyl group contains heteroatoms, the heteroatoms may form one or more functional groups well-known to one skilled in the art. Hydrocarbyl groups may contain cycloaliphatic, aliphatic, aromatic, or any combination of such segments. The aliphatic segments can be straight or branched. The aliphatic and cycloaliphatic segments may include one or more double and/or triple bonds. Included in hydrocarbyl groups are alkyl, alkenyl, alkynyl, aryl, cycloalkyl, cycloalkenyl, alkaryl, and aralkyl groups. Cycloaliphatic groups may contain both cyclic portions and noncyclic portions. Hydrocarbylene means a hydrocarbyl group or any of the described subsets having more than one valence, such as alkylene, alkenylene, alkynylene, arylene, cycloalkylene, cycloalkenylene, alkarylene and aralkylene. As used herein percent by weight or parts by weight refer to, or are based on, the weight or the compounds or compositions described unless otherwise specified.

The term "ketal" refers to a molecule having a ketal functionality; i.e., a molecule containing a carbon bonded to two —OR groups, where O is oxygen and R represents any alkyl group or hydrogen. The terms "volatile" and "non-volatile" refers to a compound which is capable of evaporating readily at normal temperatures and pressures, in the case of volatile; or which is not capable of evaporating readily at normal temperatures and pressures, in the case of non-volatile. As used herein, the term "stabilized" (e.g., in the context of "stabilized" 1,1-disubstituted alkene compounds or compositions comprising the same) refers to the tendency of the compounds (or their compositions) to substantially not polymerize with time, to substantially not harden, form a gel, thicken, or otherwise increase in viscosity with time, and/or to substantially show minimal loss in cure speed (i.e., cure speed is maintained) with time.

The starting 1,1-disubstituted alkene compound preferably is prepared using a method which results in a sufficiently high purity so that it can be polymerized. The purity of the 1,1-disubstituted alkene compound may be sufficiently high so that 70 mole percent or more, preferably 80 mole percent or more, more preferably 90 mole percent or more, even more preferably 95 mole percent or more, and most preferably 99 mole percent or more of the 1,1-disubstituted alkene compound is converted to polymer during a polymerization process. The purity of the 1,1-disubstituted alkene compound preferably is about 85 mole percent or more, more preferably about 90 mole percent or more, even more preferably about 93 mole percent or more, even more preferably about 95 mole percent or more, even more preferably about 97 mole percent or more, and most preferably about 99 mole percent or more, based on the total weight of the 1,1-disubstituted alkene compound. If the 1,1-disubstituted alkene compound includes the analogous 1,1-disubstituted alkane impurity it should preferably be about 10 mole percent or less, or more preferably about 1 mole percent or less. The concentration of any impurities containing a dioxane group preferably is about 2 mole percent or less, more preferably about 1 mole percent or less, even more preferably about 0.2 mole percent or less, and most preferably about 0.05 mole percent or less, based on the total weight of the 1,1-disubstituted alkene compound. The total concentration of any impurity having the alkene group replaced by an analogous hydroxyalkyl group (e.g., by a Michael addition of the alkene with water) preferably is about 3 mole percent or less, more preferably about 1 mole percent or less, even more preferably about 0.1 mole percent or less, and most preferably about 0.01 mole percent or less, based on the total moles in the 1,1-disubstituted alkene compound. Preferred 1,1-disubstituted alkene compounds are prepared by a process including one or more (e.g., two or more) steps of distilling a reaction product or an intermediate reaction product (e.g., a reaction product or intermediate reaction product of a source of formaldehyde and a malonic acid ester).

The hydrocarbyl moieties on the ester groups must be capable of transesterifying under the conditions of the method disclosed herein and contain functional groups that may be reactive under typical transesterification conditions. The first ester compound can be a monofunctional ester having bonded to the carbonyl group of the ester group a hydrocarbyl group. In some embodiments the first ester compound is a compound with multiple functional groups that may be reactive under typical transesterification conditions, at least one of the functional groups is an ester group. Any compounds that have one or more ester groups and another functional groups that may react under typical transesterification conditions may be the first ester compound that is subject to transesterification according to the processes disclosed herein. Included in functional groups that can undergo side reactions under transesterification conditions are unsaturated groups, especially those that are adjacent to one or more electron withdrawing groups; i.e., α, β-unsaturated monoester or α, β-unsaturated 1,1-diester or α, β-unsaturated-1-cyano-1-ester, and the like. Exemplary side reactions include addition polymerization, by anionic or free radical polymerization, Michael addition of alcohols to unsaturated groups, and the like. Exemplary classes of compounds include 1,1-disubstituted alkenes, cyanoacrylates, acrylates, methacrylates, and the like. The product of the method of the invention preferably contains a low amount of byproducts such as Michael addition products or polymerization products. In some embodiments the total concentration of any impurity having the alkene group replaced by an analogous hydroxyalkyl group (e.g., by a Michael addition of the alkene with water), preferably is about 3 mole percent or less, more preferably about 1 mole percent or less, even more preferably about 0.1 mole percent or less, and most preferably about 0.01 mole percent or less, based on the total moles in the transesterified 1,1-disubstituted alkene compound. In some embodiments the total concentration of any impurity formed by polymerization is preferably about 1 mole percent or less, more preferably about 0.5 mole percent or less, even more preferably about 0.1 mole percent or less, and most preferably about 0.01 mole percent or less, based on the total moles in the transesterified 1,1-disubstituted alkene compound.

A preferred class of 1,1-disubstituted alkene compounds are the methylene malonates which refer to compounds having the following representative formula:

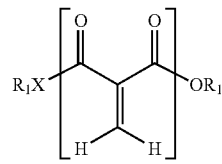

Transesterification is an equilibrium process and is typically performed under conditions to remove the byproduct formed during the exchange, meaning the product formed by the hydrocarbyl moieties leaving the esters undergoing transesterification. In some desired embodiments the hydrocarbyl moieties leaving the ester group of the first ester compound are smaller than the hydrocarbyl moieties replacing them so as to make the byproducts more volatile than the transesterified first ester compound. The smaller byproducts will generally be more volatile than the transesterified first ester compound, which facilitates removal of the byproduct due to their volatile nature. The process disclosed can be used with any process conditions that remove the byproduct formed from the leaving hydrocarbyl moieties. Exemplary process conditions or steps that may be used to remove the byproduct formed from the leaving hydrocarbyl moieties may include one or more of the following: distillation, membrane transport, inert gas purge, and the like.

In some embodiments disclosed is a method of transesterifying one or more ester groups of one or more 1,1-disubstituted alkene compounds by contacting with one or more alcohols having one or more hydroxyls or one or more second ester compounds in the presence of an acid catalyst or ester thereof, for instance a super acid or ester thereof, under conditions such that one or more of the esters of the 1,1-disubstituted alkene compounds undergo transesterification. In essence the alcohol hydrocarbon backbone replaces the hydrocarbyl moiety or the hydrocarbyl moiety on the second ester replaces the hydrocarbyl moiety on the first ester compound. The resulting product comprises one or more 1,1-disubstituted alkene compounds having one or more of the hydrocarbyl moieties replaced. A mixture of alcohols and or second ester compounds may be used to prepare a mixture of compounds. Where the alcohol or second ester compound is multifunctional (i.e., has more than one hydroxyl group or ester group) the resulting product will contain a number of difunctional and/or multifunctional compounds. Where the alcohols or second esters comprise a mixture of monofunctional compounds, having one hydroxyl group or ester group and polyfunctional alcohols or second esters, the resulting products will be a mixture of monofunctional compounds and difunctional and/or polyfunctional compounds. In some embodiments the process is illustrated by Equations 1 and 2.

In embodiments wherein the alcohol or second ester compound are multifunctional the resulting product can have one or more of the alcohol or hydrocarbyl moieties from an ester groups replaced with a core unit of the first ester. Thus all of the hydroxyl groups of the alcohol or hydrocarbyl groups of the second ester compound may be replaced with the core unit of the first ester compound or only some of them may be replaced. In the latter case the resulting compounds may have both ester terminal groups and hydroxyl terminal groups or terminal groups based on the unreacted portion of the multifunctional second ester compound. Equations 3 and 4 illustrate these reactions:

EQ3

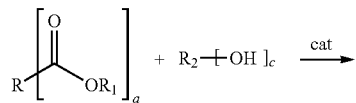

-continued

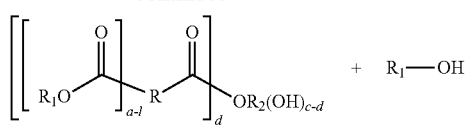

EQ4

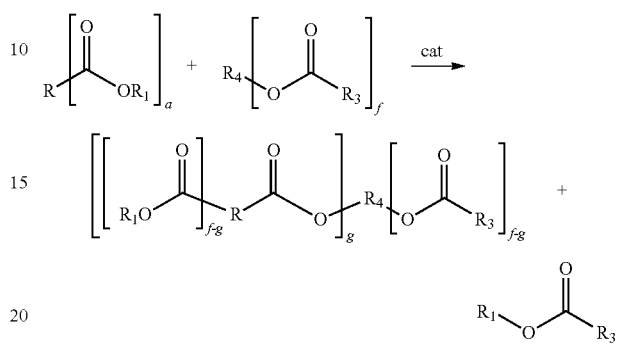

wherein R, $R_1$, $R_3$, and a are as described hereinbefore; c is separately in each occurrence, an integer of 2 or more; d is separately in each occurrence an integer of 1 or more and is equal to or less than c; f is separately in each occurrence an integer of 2 or greater and g is an integer of 1 or greater with the proviso that g must be less than f and is equal to or less than a. $R_4$ is separately in each occurrence an f-valent hydrocarbyl group.

In some embodiments of the first ester compound is a 1,1-disubstituted alkene compound where a is 2 and R is

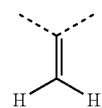

In this embodiment the processes disclosed are illustrated by the equations 5 to 8:

EQ5

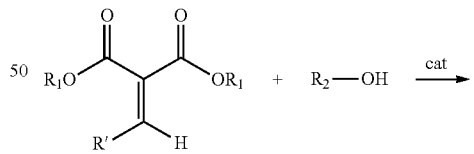

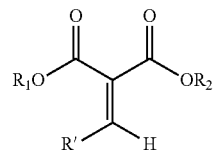

or     + $R_1$—OH

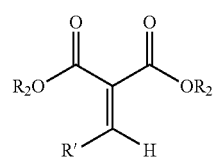

EQ6

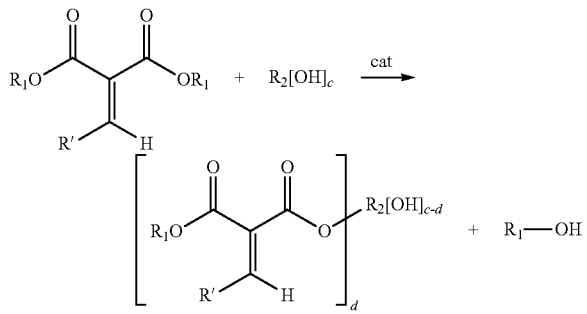

EQ7

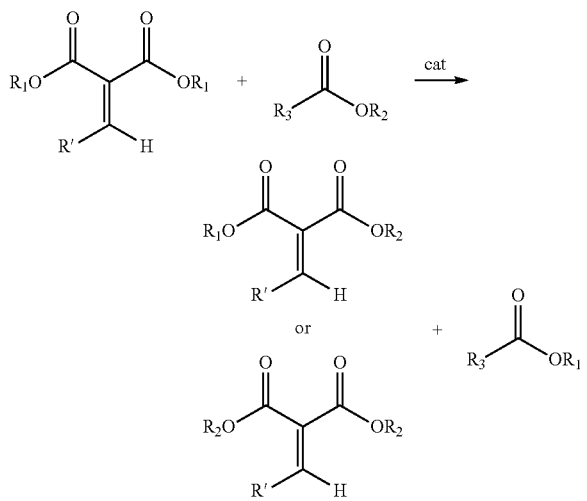

EQ8

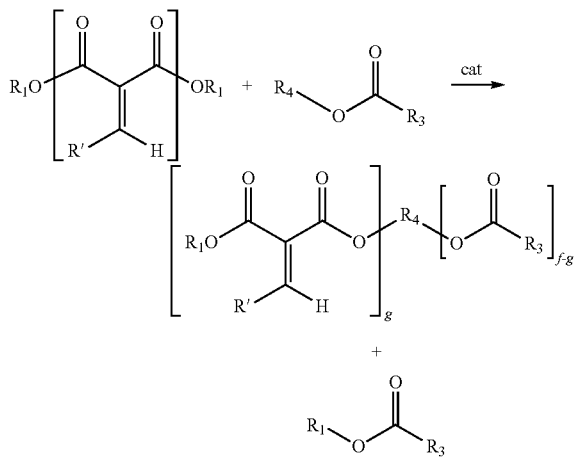

Preferably as used herein R' is hydrogen, alkyl or alkylene group. Preferably R' is hydrogen or $C_{1-10}$ alkyl or alkylene. More preferably R' is hydrogen of $C_{1-4}$ alkyl or alkylene. R' is more preferably hydrogen or alkyl. Most preferably R' is hydrogen. In the embodiment where R' is hydrogen the compounds are commonly referred to a methylene malonates.

$R_1$ is separately in each occurrence a group that can undergo replacement or transesterification under the conditions of the method disclosed herein. Preferably $R_1$ is separately in each occurrence alkyl, alkenyl, $C_3$-$C_9$ cycloalkyl, heterocyclyl, alkyl heterocyclyl, aryl, aralkyl, alkaryl, heteroaryl, or alkheteroaryl, or polyoxyalkylene, or both of the $R^1$s form a 5-7 membered cyclic or heterocyclic ring. More preferably $R_1$ is separately in each occurrence $C_1$-$C_{15}$ alkyl, $C_2$-$C_{15}$ alkenyl, $C_3$-$C_9$ cycloalkyl, $C_{2-20}$ heterocyclyl, $C_{3-20}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene, or both of the $R_1$ groups form a 5-7 membered cyclic or heterocyclic ring. The recited groups may be substituted with one or more substituents, which do not interfere with the transesterification reaction. Preferred substituents include halo alkylthio, alkoxy, hydroxyl, nitro, azido, cyano, acyloxy, carboxy, or ester. More preferably $R_1$ is separately in each occurrence $C_1$-$C_{15}$ alkyl, $C_3$-$C_6$ cycloalkyl, $C_{4-18}$ heterocyclyl, $C_{4-18}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene. More preferably $R^1$ is separately in each occurrence a $C_{1-4}$ alkyl. Most preferably $R^1$ is separately in each occurrence methyl or ethyl. Most preferably the $R^1$ is the same for each ester group on the 1,1-disubstituted alkene compounds. More preferred compounds are dimethyl, diethyl, ethylmethyl, dipropyl, dibutyl, diphenyl, and ethyl-ethylgluconate malonates. Most preferred compounds are dimethyl and diethyl methylene malonate (R is hydrogen and $R_1$ is either methyl or ethyl).

Cyanoacrylates are acrylate compounds having a cyano group double bond and acrylate ester bonded to a carbon atom. Cyanoacrylates correspond to the formula:

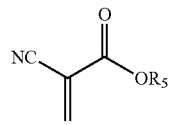

wherein $R_5$ is separately in each occurrence $C_{1-15}$ alkyl, alkoxyalkyl, cycloalkyl, alkenyl, aralkyl, aryl, allyl or haloalkyl groups. Exemplary cyanoacrylates are selected from methyl cyanoacrylate, ethyl-2-cyanoacrylate, propyl cyanoacrylates, butyl cyanoacrylates (such as n-butyl-2-cyanoacrylate), octyl cyanoacrylates, allyl cyanoacrylate, β-methoxyethyl cyanoacrylate and combinations thereof. A particularly desirable one is ethyl-2-cyanoacrylate. In some embodiments, $R_5$ is separately in each occurrence $C_{1-8}$ alkyl, alkoxyalkyl, $C_{1-8}$ alkenyl or allyl groups. In some embodiments, $R_5$ is separately in each occurrence methyl, ethyl, propyl, butyl, octyl, allyl, and β-methoxyethyl.

The alcohols can be one or more alcohols capable of transesterifying or replacing the hydrocarbon moieties on the 1,1-disubstituted alkene compounds. The alcohols can be monofunctional, one hydroxyl group, or polyfunctional, more than one hydroxyl group. Preferably the alcohol may have from 1 to 10 hydroxyl groups, more preferably 1 to 4 hydroxyl groups and most preferably 1 to 3 hydroxyl groups. Monofunctional alcohols are utilized when monofunctional compounds are the desired product. Polyfunctional alcohols are utilized when difunctional or polyfunctional products are desired. A mixture of alcohols may be used where a mixture of products is desired. Preferably the alcohols correspond to the formula $R_2$—$(OH)_c$ wherein $R_2$ may be any group that can transesterify a 1,1-disubstituted alkene compound, that is replace the hydrocarbyl moiety. Preferably $R_2$ is, separately in each occurrence, alkyl, alkenyl, $C_3$-$C_9$ cycloalkyl, heterocyclyl, alkyl heterocyclyl, aryl, aralkyl, alkaryl, heteroaryl, or alkheteroaryl, or polyoxyalkylene. More preferably $R_2$ is separately in each occurrence $C_1$-$C_{15}$ alkyl, $C_2$-$C_{15}$ alkenyl, $C_3$-$C_9$ cycloalkyl, $C_{2-20}$ heterocyclyl, $C_{3-20}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene. The recited groups may be substituted with one or more substituents which do not interfere with the transesterification reaction. Preferred substituents include halo alkylthio, alkoxy, hydroxyl, nitro, azido, cyano, acyloxy, carboxy, or ester. More preferably $R_2$ is separately in each occurrence $C_1$-$C_{15}$ alkyl, $C_3$-$C_6$ cycloalkyl, $C_{4-18}$ heterocycyl, $C_{4-18}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene. Where the alcohol is polyfunctional each of the recited possibilities of $R_2$ may be used with a bond for each of the hydroxyl groups, for instance if the alcohol has three hydroxyl groups then the recited core will have three bonds for each hydroxyl group. More preferably $R_2$ is one or more $C_{1-4}$ alkyl groups different than the hydrocarbyl moiety of the ester group, a cycloalkyl group, an alkyl substituted cycloalkyl group, a cycloalkyl substituted alkyl group, an alkaryl group, an aralkyl group or a polyoxyalkylene group which may be substituted with any substituent that does not interfere with the diester ligand replacement. Most preferably $R_2$ is, separately in each occurrence, methyl or ethyl, which is different than the diester ligand, $C_{3-8}$ alkyl, cyclohexyl, fenchyl, $C_{7-18}$ alkaryl poly-yl, or $C_{7-18}$ alkyl cycloalkyl poly-yl. In the embodiment wherein the alcohol is multifunctional, $R_2$ may be a $C_{1-15}$ alk-polyl, a $C_{3-8}$ cycloalk-polyl; a polyoxyalkylene oxide containing a number of branches and ether units, $C_{7-18}$ alkyl cycloalkyl. Among preferred alkaryl polyols are polyols with the structure of -aryl-alkyl-aryl- (such as -phenyl-methyl-phenyl- or -phenyl-propyl-phenyl-) and the like. In some embodiments c is an integer of 20 or less, 10 or less, 4 or less, 3 or less or 2 or less. Among preferred alkyl cycloalkyl poly-yls are those with the structure of -cycloalkyl-alkyl-cycloalkyl- (such as -cyclohexyl-methyl-cyclohexyl- or -cyclohexyl-propyl-cyclohexyl-) and the like. In some embodiments the alcohol can be multifunctional and contain other functional groups such as acrylate groups. In some embodiments the alcohol can be one or more hydroxyl alkyl (meth)acrylates and may contain more than one hydroxyl and or (meth) acrylate group. Exemplary hydroxyl alkyl (meth)acrylate groups include hydroxyethyl acrylate, hydroxyethyl methacrylate, 3-hydroxypropyl methacrylate, hydroxyhexyl acrylate, hydroxyoctyl methacrylate, hydroxybutyl methacrylate, hydroxybutylacrylate, 3-hydroxypentyl acrylate, 6-hydroxynonyl acrylate, 3-hydroxypropyl methacrylate, 2-hydroxypentyl methacrylate, 5-hydroxypentyl methacrylate, 7-hydroxyheptyl methacrylate, 5-hydroxydecyl methacrylate, diethylene glycol monoacrylate, diethylene glycol monomethacrylate, glycerin dimethacrylate, tri-methylol propane dimethacrylate, alkoxylated hydroxyethyl acrylate, trimethylolpropane diacrylate, alkoxylated trimethylolpropane diacrylate, reaction products of polyether glycols of acrylic or methacrylic acid, the monoacrylate or monomethacrylate esters of bisphenol-A, the fully hydrogenated derivative of bisphenol-A, cyclohexyl diol, and the like. More preferably the compounds containing one or more active hydrogen containing groups and one or more acrylate groups include hydroxymethyl (meth)acrylate, 2-hydroxyethyl hydroxyethyl (meth)acrylate, hydroxylpropyl (meth) acrylate, and 2-hydroxy propyl (meth)acrylate. In some embodiments the alcohols are primary or secondary alcohols. In some embodiments the alcohols are primary.

In the context of this disclosure the second ester compound is an ester compound that provides a hydrocarbyl moiety or hydrocarbon backbone to replace a hydrocarbyl moiety on the first ester compound. Generally the hydrocarbyl moiety or backbone of the second ester compound is different than the hydrocarbyl moiety leaving the first ester compound. In some embodiments the hydrocarbyl moiety from the second ester compound is larger than the leaving moiety from the first ester compound so that the byproduct formed by the leaving hydrocarbyl moiety is more volatile than the other compounds in the reaction mixture; for instance, the second ester, first ester, and the transesterification product. This higher volatility facilitates removal of the byproduct so as to push the equilibrium in the direction of the desired transesterification product. The second ester can be illustrated by the following formulas:

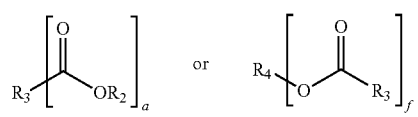

wherein $R_2$ and a are as described hereinbefore, $R_3$ is a hydrocarbyl group, and $R_4$ is an f-valent hydrocarbyl group. Preferably $R_3$ is, separately in each occurrence, hydrogen, alkyl, alkenyl, $C_3$-$C_9$ cycloalkyl, heterocyclyl, alkyl heterocyclyl, aryl, aralkyl, alkaryl, heteroaryl, or alkheteroaryl, or polyoxyalkylene. More preferably $R_3$ is separately in each occurrence hydrogen, $C_1$-$C_{15}$ alkyl, $C_2$-$C_{15}$ alkenyl, $C_3$-$C_9$ cycloalkyl, $C_{2-20}$ heterocyclyl, $C_{3-20}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene. Even more preferably $R_3$ is separately in each occurrence hydrogen or $C_1$-$C_{15}$ alkyl. Even more preferably $R_3$ is separately in each occurrence hydrogen or $C_1$-$C_4$ alkyl. Most preferably $R_3$ is separately in each occurrence hydrogen or methyl. The recited groups may be substituted with one or more substituents which do not interfere with the transesterification reaction, such as disclosed hereinbefore. Preferably $R_4$ is, separately in each occurrence, an f-valent alkyl, alkenyl, $C_3$-$C_9$ cycloalkyl, heterocyclyl, alkyl heterocyclyl, aryl, aralkyl, alkaryl, heteroaryl, or alkheteroaryl, or polyoxyalkylene group. More preferably $R_4$ is, separately in each occurrence, an f-valent $C_1$-$C_{15}$ alkyl, $C_2$-$C_{15}$ alkenyl, $C_3$-$C_9$ cycloalkyl, $C_{2-20}$ heterocyclyl, $C_{3-20}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene. Most preferably $R_4$ is separately in each occurrence an f-valent $C_1$-$C_{15}$ alkyl or polyoxyalkylene polyol. Preferred substituents include halo alkylthio, alkoxy, hydroxyl, nitro, azido, cyano, acyloxy, carboxy, or ester. More preferably $R_2$ is, separately in each occurrence, $C_1$-$C_{15}$ alkyl, $C_3$-$C_6$ cycloalkyl, $C_{4-18}$ heterocyclyl, $C_{4-18}$ alkheterocyclyl, $C_{6-18}$ aryl, $C_{7-25}$ alkaryl, $C_{7-25}$ aralkyl, $C_{5-18}$ heteroaryl or $C_{6-25}$ alkyl heteroaryl, or polyoxyalkylene. In some embodiments a is an integer of 20 or less, 10 or less, 4 or less, 3 or less or 2 or less. In some embodiments f is an integer of 20 or less, 10 or less, 4 or less, 3 or less or 2 or less. Exemplary classes of second esters include hydrocarbyl carboxylates, hydrocarbyl acetates, hydrocarbyl formates, and the like. Among second esters that may be used in certain embodiments are hydrocarbyl acetates, hydrocarbyl formates, and the like. In some embodiments the hydrocarbyl groups on the second esters are alkyls, alkenyl, alkaryl or cycloalkyl substituted alkyl. Among second esters that may be used in certain embodiments are hydrocarbyl acetates, for instance butyl acetate, isobutyl acetate, tert-butyl acetate, pentyl acetate, isopentyl acetate, prenyl acetate, allyl acetate, benzyl acetate, diethylene glycol diacetate, triethylene glycol diacetate, and the like. Among second esters that may be used in certain embodiments are hydrocarbyl formates, for instance butyl formate, isobutyl formate, pentyl formate, isopentyl formate, hexyl formate, heptyl formate, phenyl formate, phenethyl formate, anisyl formate, benzyl formate, and the like.

In the context of the equations presented herein in some embodiments c and f can be separately in each occurrence an integer of 20 or less, 10 or less, 4 or less, or 3 or less.

Where the process is performed using a second ester compound, for instance an acetate or formate, the formation of Michael addition products is minimized or eliminated in the transesterification process. Preferably the total concentration of any impurity having the alkene group replaced by an analogous hydroxyalkyl group (e.g., by a Michael addition of the alkene with water), preferably is about 3 mole percent or less, more preferably about 2 mole percent or less, even more preferably about 1 mole percent or less, and most preferably about 0.5 mole percent or less, based on the total moles in the 1,1-disubstituted alkene compound.

The catalyst is an acid or an ester thereof. Any acid or ester thereof that catalyzes transesterification while minimizing side reactions may be used. In some embodiments the acid or acid utilized to form an ester is an acid having a pKa in a polar aprotic solvent, such as acetonitrile or dioxane, as disclosed hereinafter. In particular the pKa is chosen to efficiently catalyze the transesterification reaction while minimizing side reaction and the concentration of catalyst in a reaction mixture. In some embodiments the acid used has a pKa of about −5 or greater, more preferably about −3 or greater, and most preferably about 1.0 or greater. In some embodiments the acid used has a pKa of about 14 or less, more preferably about 11 or less, and most preferably about 9 or less. The acid can be a Bronsted acid having a pKa as disclosed. In some embodiments the catalyst is a superacid or an ester thereof. Superacid means an acid having an acidic strength greater than the strength of 100 percent sulfuric acid. Ester thereof, in the context of the acid catalysts, refer to compounds wherein the hydrogen on the acid is replaced with a hydrocarbyl group, preferably an alkyl group.

Superacids are acids having a strength greater than the strength of 100 percent sulfuric acid, a pKa less than 100 percent sulfuric acid, that is less than 8, more preferably less than about 5, and most preferably less than about 2. The measurement of acid strength is based on Kutt et al. "Equilibrium Acidities of Super Acids," Journal of Organic Chemistry Vol 76 pages 391 to 395, 2011, published on the Web Dec. 17, 2010, which is incorporated herein by reference. Preferred super acids include trifluoromethanesulfonic acid (triflic acid), sulfated tin oxide, triflated tin oxide, sulfated zirconia, triflated zirconia, and triflated HZSM-5. The most preferred super acids are triflic acid and fluorosulfonic acid.

Preferred acid catalysts include triflic acid, fluorosulfonic acid, and sulfuric acid. For reactions requiring monosubstitution (only one hydroxyl group on the alcohol or one ester group on the second ester is being replaced by transesterification), weaker acids with pKa values equal to or higher than sulfuric acid may be desired. Examples of such acids include sulfuric acid or methanesulfonic acid. For reactions requiring disubstitution (two hydroxyl groups on the alcohol or two ester groups on the second ester are being replaced by transesterification), stronger acids with pKa values equal to or lower than sulfuric acid may be desired. Examples of such acids include sulfuric acid, fluorosulfonic acid, and triflic acid. For reactions requiring polysubstitution (more than 2 hydroxyl groups on the alcohol and more than 2 ester groups on the second ester compound), choice of acid catalysts can be similar to that for disubstitution reactions but reaction time may need to be increased. Preferred esters of acids useful as catalysts include alkyl triflates.

The catalyst can be mixed with the reactants or can be supported on a substrate such as a membrane or an inert carrier such as a porous support structure (the catalysts can be heterogeneous). Catalysts which are not supported are commonly referred to as homogeneous. The catalyst can be used in any concentration that catalyzes the reaction of alcohols or the second ester compounds with the first ester compound, such as 1,1-disubstituted alkene compounds, to replace the hydrocarbyl moiety on an ester group. The amount of catalyst utilized for the reaction depends on the type of catalyst being chosen and the desired level of substitution of the hydroxyl groups in the alcohol or ester groups in the second ester compound. Preferably the concentration of catalyst is about 0.1 molar equivalents or less per equivalent of the first ester compound; more preferably about 0.01 molar equivalents or less; even more preferably about 0.009 molar equivalents or less; and more preferably about 0.006 molar equivalents or less. Preferably the concentration of catalyst is about 0.001 molar equivalents or greater per equivalent of the first ester compound; and most preferably about 0.0015 molar equivalents or greater. Higher concentrations of catalysts than recited may be utilized. As disclosed in Malofsky et al., U.S. Pat. Nos. 8,609,885 and 8,884,051; and Malofsky et al. WO 2013/059473 the presence of acid in the 1,1-disubstituted alkene compounds recovered can present problems with respect to use of the compounds and low concentrations of acid in the products in use is desired. If high levels of acid are contained in the final product, additional purification or removal steps may be required. The preferred amounts recited achieve the balance between efficient catalysis and the need for low acid concentrations in the product for use. In embodiments when the catalyst is selected from sulfuric acid or those acids having pKa values greater than that of sulfuric acid, the concentration of such catalysts in the reaction mixture is preferably at the upper end of the ranges recited herein The choice of alcohol and/or second ester compound and the relative moles of alcohol and/or second ester compound to the first ester compound, such as a 1,1-disubstituted alkene compound, will impact the product of the process. To prepare symmetric 1,1-disubstituted alkene compounds it is desirable to replace all of the hydrocarbyl moieties on the 1,1-disubstituted alkene compounds and the molar ratio is chosen to achieve this result. Preferably the molar ratio of alcohol and/or second ester compound to 1,1-disubstituted alkene compounds is about 2:1 or greater and preferably about 4:1 or greater in embodiments where preparation of symmetrical products is desired. In embodiments where in the alcohol or second ester compound is polyfunctional it is desirable to react all of the hydroxyl groups or ester oxygen of the second ester and the molar ratio of such compounds to 1,1-disubstituted alkene compounds is chosen to achieve this result and the equivalents ratio is chosen such that there is an excess of 1,1-disubstituted alkene compounds. Preferably the mole ratio of polyfunctional alcohol or second ester compound to 1,1-disubstituted alkene compounds is about 1:2 or less and more preferably about 1:3 or less. To prepare asymmetric 1,1-disubstituted alkene compounds the molar equivalents of monofunctional alcohol or second ester compound to 1,1-disubstituted alkene compounds are chosen so as to result the desired product and it is believed that expected statistical results can be achieved.

Where the reactants are liquid under reaction conditions it is desired to contact the reactants and catalysts in neat form (i.e., without a solvent or dispersant). If the use of a solvent is desired, a solvent that does not react with the reactants or the catalyst is preferred. Another consideration in the choice of solvents is the boiling point of the solvent chosen. It is desired that the solvent have a boiling point of about 15° C., preferably about 20° C., or higher than the temperature at which the reaction is conducted. Aprotic solvents are preferred and more preferred solvents are long chain alkanes having a boiling point above the reaction temperature as described herein; exemplary solvents are decane or dodecane.

The reactants are contacted at any temperature at which the transesterification will proceed. Preferably the reactants are contacted at a temperature of about 80° C. or greater and most preferably about 100° C. or greater. Preferably the reactants are contacted at a temperature of about 160° C. or less, even more preferably 140° C. or less, and most preferably about 130° C. or less.

The reactants are contacted for a sufficient time to prepare the desired transesterified product. It is preferred to perform the process such that the starting first ester compound, such as a 1,1-disubstituted alkene compound, is substantially completely reacted with the alcohol or second ester compound to prepare the desired product. Preferably the reactants are contacted for about 1 hour or greater. Preferably the reactants contacted is 4 hours or less and more preferably about 2 hour or less.

It is desired to perform the process under conditions that enhance contact of the 1,1-disubstituted alkene compound and the alcohol or second ester compound to allow the replacement of the original hydrocarbyl moieties on the ester groups. Some form of agitation is desired to enhance this contact. Exemplary methods of agitation include the use of stirrers, sparging with an inert gas, and the like. A preferred method is to use vigorous stirring and/or vigorous sparging with nitrogen. The transesterification reaction is believed to be an equilibrium reaction. Performing the process under conditions to drive the reaction in the direction of the desired product is recommended. Exemplary ways to achieve this include adding an excess of one reactant, removing the alcohol or ester byproduct formed by the leaving hydrocarbyl moiety, and the like. In embodiments wherein the second alcohol or third ester compound formed from the leaving hydrocarbyl moiety is volatile it can be removed through the use of a vacuum, use of conditions at which the leaving alcohol or ester can be distilled off and the other reactants and products do not distill away.

The alcohols or the second ester compound and the first ester compound, such as 1,1-disubstituted alkene compounds, may be reacted in the presence of free radical stabilizers and anionic polymerization inhibitors as described in Malofsky et al., U.S. Pat. Nos. 8,609,885 and 8,884,051; and Malofsky et al. WO 2013/059473, relevant parts incorporated herein by reference. In some embodiments, to prevent production of polymeric products, it is desirable to include an acid which inhibits polymerization but does not significantly participate in catalysis of the transesterification. Preferably the acid used to inhibit polymerization has a pKa greater than 100 percent sulfuric acid. According to certain embodiments, stabilizers can be included in compositions containing the transesterified products to increase and improve the shelf life and to prevent spontaneous polymerization. Generally, one or more anionic polymerization stabilizers and or free-radical stabilizers may be added to the compositions. Anionic polymerization stabilizers are generally electrophilic compounds that scavenge electrons from the composition or growing polymer chain. The use of anionic polymerization stabilizers can terminate additional polymer chain propagation. Exemplary anionic polymerization stabilizers are acids, exemplary acids are carboxylic acids, sulfonic acids, phosphoric acids, and the like. Exemplary stabilizers include liquid phase stabilizers (e.g., methanesulfonic acid ("MSA")) and vapor phase stabilizers (e.g., trifluoroacetic acid ("TFA")). In some embodiments it is desirable to utilize relatively weak acids to inhibit polymerization. Generally such weak acids exhibit a pKa in acetonitrile of greater than −1.5 and more preferably greater than about 2. Among preferred acids used to inhibit anionic polymerization are alkyl substituted aryl sulfonic adds, such as dodecylbenzenesulfonic acid, p-toluenesulfonic acid, and the like. As the catalyst in the method of the invention is an acid a second anionic polymerization inhibitor may not be required in performing the method disclosed herein. It is desired to include a free radical stabilizer or polymerization inhibitor in performing the method disclosed herein. The concentrations of the stabilizers, or polymerization inhibitors, useful in the method are disclosed hereinafter.

Free radical stabilizers preferably include phenolic compounds (e.g., 4-methoxyphenol, mono methyl ether of hydroquinone ("MeHQ") butylated hydroxytoluene ("BHT")). Stabilizer packages for 1,1-disubstituted alkenes are disclosed in U.S. Pat. No. 8,609,885 and U.S. Pat. No. 8,884,051, each incorporated by reference. Additional free radical polymerization inhibitors are disclosed in U.S. Pat. No. 6,458,956 and are hereby incorporated by reference. Generally, only minimal quantities of a stabilizer are needed and, in certain embodiments only about 5000 parts-per-million ("ppm") or less can be included. In certain embodiments, a blend of multiple stabilizers can be included; for example, a blend of anionic stabilizers (MSA) and free radical stabilizers (MeHQ).

The one or more anionic polymerization stabilizers are present in sufficient amount to prevent premature polymerization. Preferably, the anionic polymerization stabilizers are present in an amount of about 1 ppm or greater based on the weight of the first ester compound (1,1-disubstituted alkene), more preferably about 5 ppm by weight or greater, and most preferably about 10 ppm by weight or greater. Preferably, the anionic polymerization stabilizers are present in an amount of about 500 ppm by weight or less based on the weight of the first ester compound (1,1-disubstituted alkene), more preferably about 250 ppm by weight or less, and most preferably about 100 ppm by weight or less. The one or more free radical stabilizers are present in sufficient amount to prevent premature polymerization. Preferably, the free radical polymerization stabilizers are present in an amount of about 10 ppm or greater based on the weight of the first ester compound (1,1-disubstituted alkene), more preferably about 100 ppm by weight or greater, and most preferably about 1000 ppm by weight or greater. Preferably, the free radical polymerization stabilizers are present in an amount of about 10,000 ppm by weight or less based on the weight of the first ester compound (1,1-disubstituted alkene), more preferably about 8000 ppm by weight or less, and most preferably about 5000 ppm by weight or less.

The process of this invention can prepare compounds and polymers which are end capped with compounds containing activated alkene groups, such as 1,1-disubstituted alkene compounds or cyanoacrylates. This process can be used to substitute the compounds containing activated alkene groups, such as 1,1-disubstituted alkene compounds, on any hydroxyl of a compound or polymer. For instance the process can prepare polyoxyalkylene compounds or polymers having their hydroxyl groups replaced with compounds containing activated alkene groups, such as 1,1-disubstituted alkene compounds. Bisphenol compounds, such as bisphenol A or F can be end-capped as described. Exemplary reactions are illustrated hereinafter.

The methods disclosed herein prepare a number of novel compounds and compositions. In some embodiments 1,1-disubstituted alkenes having one or more ester groups bonded to a hydrocarbyl backbone containing an ester

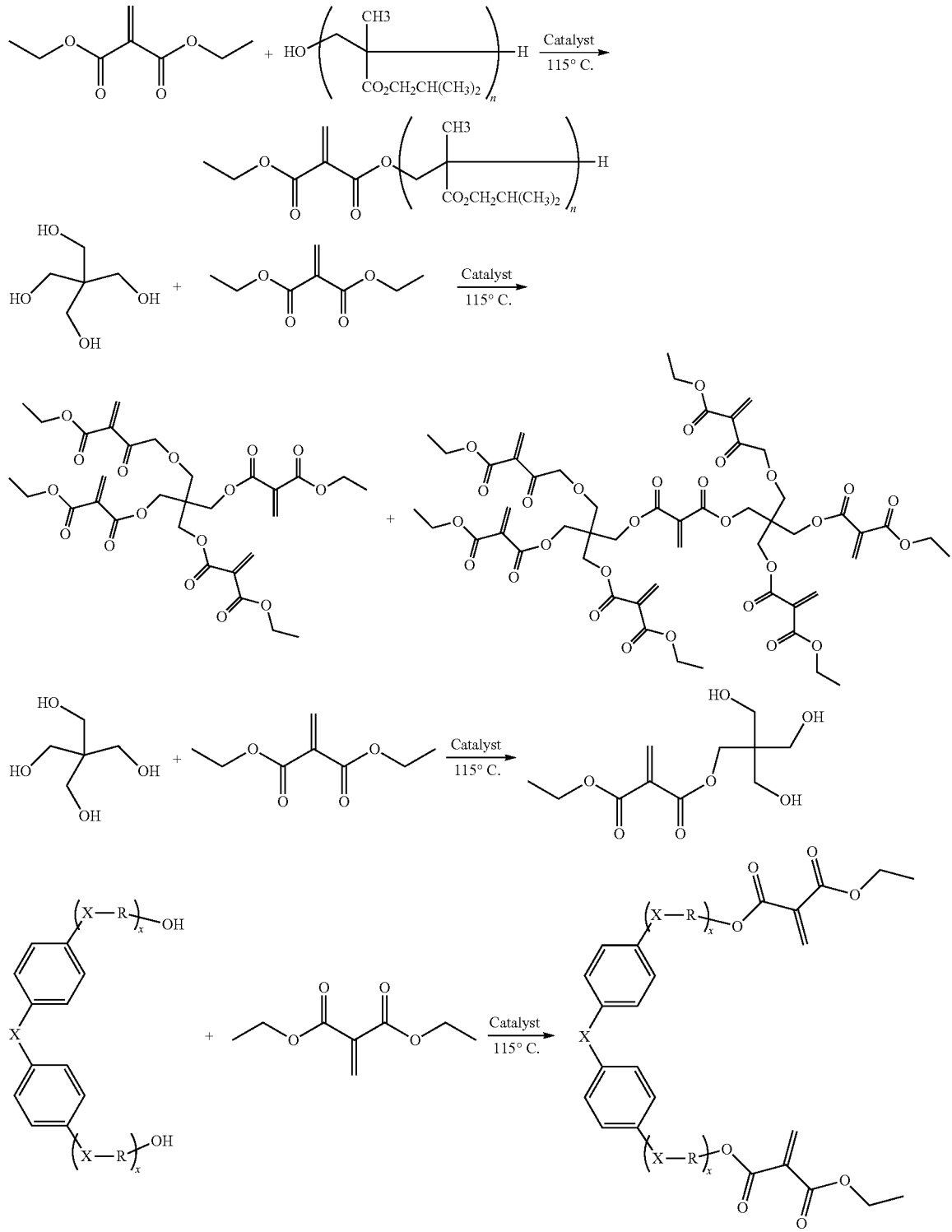

The products can be recovered by and purified by distillation as disclosed in Malofsky et al., U.S. Pat. Nos. 8,609,885 and 8,884,051.

group, such as acetate or formate group can be prepared by the method disclosed. Disclosed is a composition comprising one or more 1,1-disubstituted alkenes linked by oxygen atoms to the hydrocarbon backbone of one or more second ester compounds wherein the hydrocarbon backbone of the one or more second ester compounds is bonded to one or more ester groups. In some embodiments, the hydrocarbon back bone is bonded to an acrylate, acetate or formate group. Such compounds can be illustrated by the following formula:

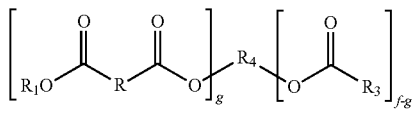

wherein f-g is 1 or greater and $R_3$ is methyl or hydrogen. In some embodiments a 1,1-disubstituted alkene can be transesterified with a hydroxyl alkyl acrylate. Where the hydroxyacrylate has 2 or more hydroxyl acrylate groups and the equivalents ratio of the 1,1-disubstituted alkene can be transesterified to the hydroxyl alkyl acrylate is less than 1 the product includes a 1,1-disubstituted alkene bonded to through an oxygen bond to the alkyl group which is further bonded to a hydroxyl alkyl acrylate. In embodiments wherein the hydroxyl alkyl acrylate contains two or more hydroxy alkyl groups and not all of the hydroxyl groups are reacted the compositions are novel. Such compounds can be represented by the following formula:

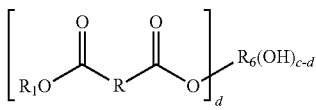

wherein, R' and $R_1$ are as described; $R_6$ is the residue of an alkyl acrylate; c is separately in each occurrence an integer of 3 or more; d is separately in each occurrence an integer of 2 or more and is less than c.

In embodiments where a mixture of monofunctional and polyfunctional alcohols or second esters are used the resulting compositions may be novel. Exemplary novel compositions include compositions comprising one or more 1,1-disubstituted alkenes and one or more compounds containing two or more core units of 1,1-disubstituted alkenes linked by oxygen atoms to the hydrocarbon backbone of one or more alcohols having two or more hydroxyl groups or the hydrocarbon backbone of one or more second ester compounds having two or more ester groups wherein the concentration of and one or more compounds containing two or more core units of 1,1-disubstituted alkenes is about 1 percent by weight or greater, in some embodiments about 5 percent by weight and in some embodiments greater than 15 percent by weight. In some embodiments the amount of multifunctional compounds can be about 50 percent by weight or less. In some embodiments the 1,1-disubstituted alkenes correspond to the formulas:

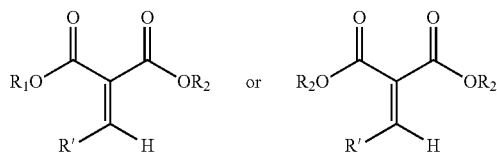

and one or more compounds containing two or more core units of 1,1-disubstituted alkenes correspond to the following formulas:

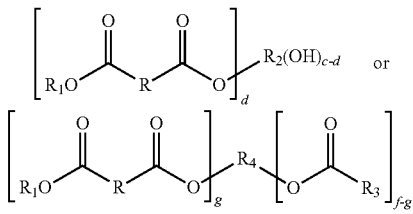

wherein: $R_1$, $R_2$, and $R_3$ are separately in each occurrence hydrocarbyl groups; $R_4$ is, separately in each occurrence, an f-valent hydrocarbyl group; R' is separately in each occurrence hydrocarbyl or hydrogen; c is, separately in each occurrence, an integer of 2 or more; d is, separately in each occurrence, an integer of 2 or more and equal to or less than c; f is, separately in each occurrence, an integer of 1 or greater and g is an integer of 2 or greater. In some embodiments the one or more compounds containing two or more core units of 1,1-disubstituted alkenes comprise a number of such compounds wherein the hydrocarbyl moieties on the terminal ester groups are different. This can occur under conditions wherein not all of the original hydrocarbyl moieties on the starting 1,1-disubstituted alkenes are replaced in the transesterification reaction. Where a mixture of mono and poly functional alcohol or second ester reagents are reacted with the 1,1-disubstituted alkenes and there is a stoichiometric excess of ester equivalents available from the 1,1-disubstituted alkenes as compared to the equivalents of the hydroxyl units of the alcohol reagent or the ester equivalents of the second ester reagents mixtures of compounds which are monofunctional and polyfunctional and contain compounds with different hydrocarbyl moieties on the ester groups can be prepared. In this embodiment, R1 is different on the same compound. In this embodiment the mixture may also contain monofunctional compounds that are asymetric, wherein the hydrocarbyl moieties on the ester groups are different, some from the starting 1,1-disubstituted alkenes and some wherein an ester exchange is completed with an alcohol reagent or a second ester reagent. In these embodiments the amount of multifunctional compounds may be greater than 1 percent by weight, more preferably 5 percent by weight or greater. In some embodiments the mixture prepared can have greater than 1 percent by weight. In some embodiments the amount of multifunctional monomer can be 50 percent by weight or less.

ILLUSTRATIVE EMBODIMENTS OF THE INVENTION

The following examples are provided to illustrate the invention, but are not intended to limit the scope thereof. All parts and percentages are by weight unless otherwise indicated.

A typical reaction procedure is described as follows: a three neck 100 mL round bottom flask with a distillation head, thermometer, vacuum adapter, and collection flask are assembled using high vacuum grade grease along with a heating mantle, thermocouple, and a magnetic stir bar. The reaction mixture is subjected to agitation typically ranging from 400-600 rpm. Vacuum is used to remove subsequent byproducts from the reaction mixture and the various pressures are indicated below along with the mix time in each case. In some cases, nitrogen gas is used to purge the mixture in lieu of vacuum and, if applicable, is indicated below. In each case, the mole equivalent is relative to the diethyl methylene malonate ("DEMM") monomer used.

NMR spectroscopy is employed using a 300 MHz NMR to analyze reaction mixtures. Samples were prepared using chloroform-d (CDCl$_3$) and hexamethyldisiloxane as an internal standard appearing at about 0 ppm. For 1,1-disubstituted alkene compounds with symmetrical substituents (e.g., DEMM), the reactive alkene functionality (i.e., the double bond) appears at about 6.45 ppm. For 1,1-disubstituted alkene compounds with asymmetrical substituents (e.g., ethyl pentyl methylene malonate or "EPMM"), the reactive alkene functionality appears as a doublet at about 6.45 ppm. In most cases, four NMR scans are run on each samples specimen with a 20 second delay between scans.

GC-MS is employed to determine conversion of starting materials to the desired transesterified product(s) and detect the presence of any byproducts. A helium gas (carrier gas) purge of about 1 mL/min is employed to aid the ionized in sample reaching the MS detector. Typical sample injection volumes of 1-2 µL of about 2-5% of the reaction mixture in dichloromethane (CH$_2$Cl$_2$) are used for injecting into the GC-MS instrument. The GC-MS profile method involves maintaining the oven at 100° C., followed by a ramp of 15° C./min to 250° C. Typical run times range from 18-23 minutes. Retention times of 1,1-disubstituted alkene compounds, based on the above mentioned method, range from 4.5-17 min and are strongly dependent on the substituents and the ease of ionization of the particular molecule in the GC chamber.

For the examples herein disclosed, the conversion of starting reactant materials (i.e., a first ester or 1,1-disubstituted alkene compound) to the desired transesterified 1,1-disubstituted alkene compounds with the use of a suitable transesterification reagent (i.e., an alcohol, acetate, or formate) is calculated as follows unless otherwise indicated: The starting weight of the limiting reagent in each reaction is used as the baseline measurement and constitutes 100% theoretical maximum conversion. Conversion is then obtained by dividing the percent composition of the transesterified product provided via GC-MS in the final reaction mixture by the theoretical maximum conversion.

Ingredients and Products
BEMM Benzyl ethyl methylene malonate (ethyl benzyl-1-methylene-1,1-dicarboxylate)
BHT Butylated hydroxytoluene
DBSA Dodecylbenzenesulfonic acid
DEMM Diethyl methylene malonate (diethyl 1-methylene-1,1-dicarboxylate)
Di-EDiEGMM Disubstituted ethyl diethylene glycol methylene malonate (ethyl diethyleneglycol-1-methylene-1,1-dicarboxylate)
Di-EHMM Disubstituted ethyl hexyl methylene malonate (ethyl hexyl-1-methylene-1,1-dicarboxylate)
EAMM Ethyl allyl methylene malonate (ethyl allyl-1-methylene-1,1-dicarboxylate)
EBMM Ethyl butyl methylene malonate (ethyl butyl-1-methylene-1,1-dicarboxylate)
EDiEGMM Ethyl diethylene glycol methylene malonate (ethyl diethyleneglycol-1-methylene-1,1-dicarboxylate)
EEmMM Ethyl ethylmethacrylate methylene malonate (ethyl ethylmethacrylate-1-methylene-1,1-dicarboxylate)
EHMM Ethyl hexanol methylene malonate (ethyl hexanol-1-methylene-1,1-dicarboxylate)
EIpMM Ethyl isopentyl methylene malonate (ethyl isopentyl-1-methylene-1,1-dicarboxylate)
EPMM Ethyl pentyl methylene malonate (ethyl pentyl-1-methylene-1,1-dicarboxylate)
EPrMM Ethyl prenyl methylene malonate (ethyl isopentenyl-1-methylene-1,1-dicarboxylate)
FEMM Fenchyl ethyl methylene malonate (ethyl fenchyl-1-methylene-1,1-dicarboxylate
HEMA Hydroxyethyl methacrylate
HEMM Ethyl hexyl methylene malonate (ethyl hexyl-1-methylene-1,1-dicarboxylate)
MeHQ Mono methyl ether hydroquinone
MEMM Menthyl ethyl methylene malonate (ethyl menthyl-1-methylene-1,1-dicarboxylate)
MePPEMM 2-Methyl-1-phenyl-2-propyl ethyl methylene malonate (2-Methyl-1-phenyl-2-propyl ethyl-1-methylene-1, 1-dicarboxylate)
MSA Methanesulfonic acid
PEMM 2-Phenyl-1-propyl ethyl methylene malonate (2-Phenyl-1-propyl-ethyl-1-methylene-1,1-dicarboxylate)
PPEMM 2-Phenyl-2-propyl ethyl methylene malonate (2-Phenyl-2-propyl-ethyl-1-methylene-1,1-dicarboxylate)
TFMSA Trifluoromethanesulfonic acid or triflic acid Example 1—Preparation of HEMM The reactor is charged with 25 g (1 equivalent) of DEMM, 5.9 g (0.4 equivalents) of hexanol, 0.82 g (0.25 equivalents) of BHT, and 0.154 g of sulfuric acid (about 5 weight percent based on DEMM and hexanol). The reaction mixture is heated to 130° C. and the ethanol byproduct is removed using about 500 mm Hg of reduced pressure. GC-MS results are obtained and used to calculate conversion: about 72.5 percent to HEMM under these conditions. This has an elution time of 8.8 minutes by GC-MS. This reaction is illustrated by the following equation:

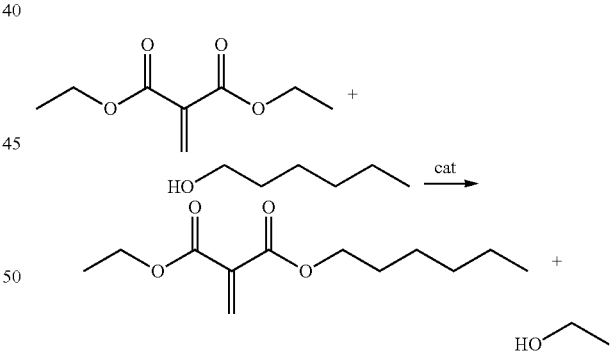

Example 2—Preparation of EEmMM

To the round bottom flask set-up, a mixture of 20 g (1 equivalent) of DEMM, 3.7792 g (0.25 equivalents) of HEMA, 1.442 g (0.1 equivalent) of MeHQ, 1.8962 g (0.05 equivalents) of DBSA, and 0.1742 (0.01 equivalents) of TFMSA is combined with agitation. Heat is applied to the reaction mixture and maintained at about 90° C. and mixed for 4 hours while vigorously purging with nitrogen gas. Ethanol is collected as the reaction byproduct GC-MS results are obtained and used to calculate conversion: 75.8 percent to EEmMM under these conditions. This has an elution time of about 9.96 minutes by GC-MS. This reaction is illustrated by the following equation:

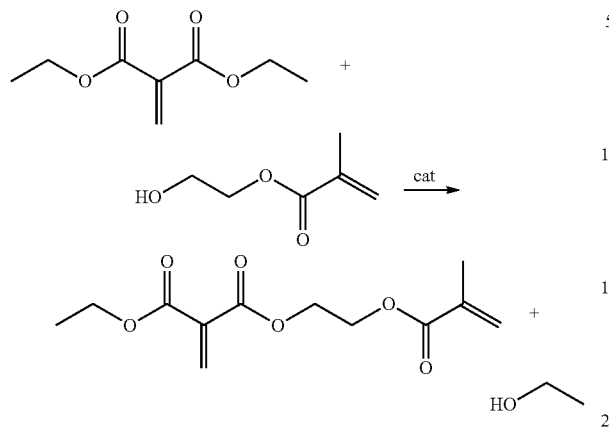

Example 3—Preparation of EPMM

To the round bottom flask set-up, a mixture of 30 g (1 equivalent) of DEMM, 7.561 g (0.33 equivalents) pentyl acetate 2.163 (0.1 equivalent) of MeHQ, 2.844 g (0.05 equivalents) of DBSA, and 0.342 (0.02 equivalents) of sulfuric acid is combined with agitation. Heat is applied to the reaction mixture and maintained at about 130° C. and mixed for 4 hours applying reduced pressure at about 450 mmHg. Ethyl acetate is collected as the reaction byproduct. GC-MS results are obtained and used to calculate conversion: 88.3% to EPMM under these conditions. This has an elution time of about 7.93 minutes by GC-MS. This reaction is illustrated by the following equation:

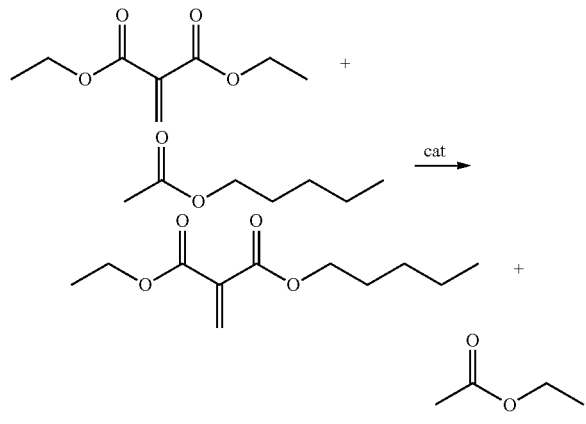

Example 4—Preparation of EPMM

To the round bottom flask set-up, a mixture of 30 g (1 equivalent) of DEMM, 5.120 g (0.33 equivalents) of pentanol, 2.163 (0.1 equivalent) of MeHQ, 2.844 g (0.05 equivalents) of DBSA, and 0.342 (0.02 equivalents) of sulfuric acid is combined with agitation. Heat is applied to the reaction mixture and maintained at about 130° C. and mixed for 4 hours applying reduced pressure at about 450 mmHg. Ethanol is collected as the reaction byproduct. GC-MS results are obtained and used to calculate conversion: 74.4% to EPMM under these conditions. This has an elution time of about 7.93 minutes by GC-MS. This reaction is illustrated by the following equation:

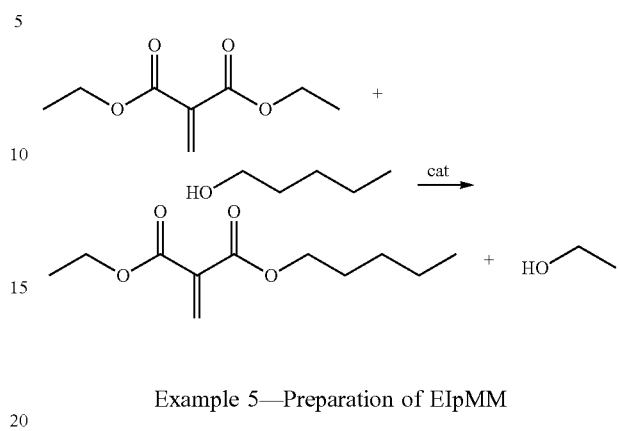

Example 5—Preparation of EIpMM

To the round bottom flask set-up, a mixture of 30 g (1 equivalent) of DEMM, 7.561 g (0.33 equivalents) of isopentyl acetate, 2.163 g (0.1 equivalent) of MeHQ, 2.844 g (0.05 equivalents) of DBSA, and 0.261 (0.01 equivalents) of TFMSA is combined with agitation. Heat is applied to the reaction mixture and maintained at about 130° C. and mixed for 3 hours applying reduced pressure at about 450 mmHg. Ethyl acetate is collected as the reaction byproduct. GC-MS results were obtained and used to calculate conversion: 65.6% to EIpMM under these conditions. This has an elution time of about 7.55 minutes by GC-MS. This reaction is illustrated by the following equation:

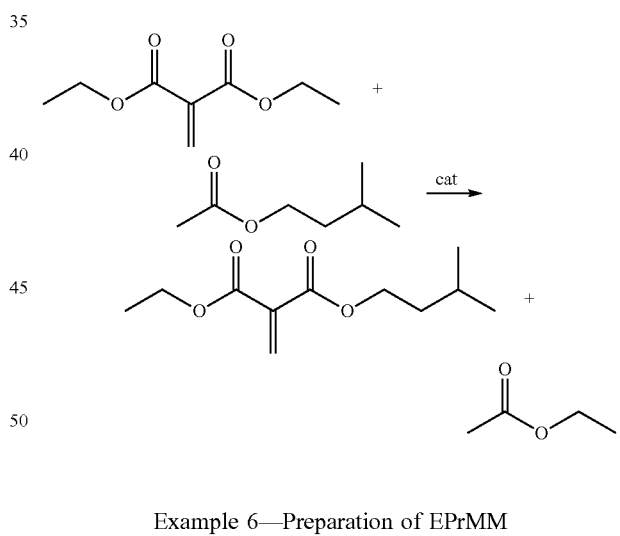

Example 6—Preparation of EPrMM

To the round bottom flask set-up, a mixture of 30 g (1 equivalent) of DEMM, 7.444 g (0.33 equivalents) of prenyl acetate, 2.163 g (0.1 equivalent) of MeHQ, 2.844 g (0.05 equivalents) of DBSA, and 0.261 (0.01 equivalent) of TFMSA is combined with agitation. Heat is applied to the reaction mixture and maintained at about 130° C. and mixed for 1 hour while applying reduced pressure at about 450 mmHg. Ethyl acetate is collected as the reaction byproduct. GC-MS results are obtained and used to calculate conversion: 53.2% to EPrMM under these conditions. This has an elution time of about 7.92 minutes by GC-MS. This reaction is illustrated by the following equation:

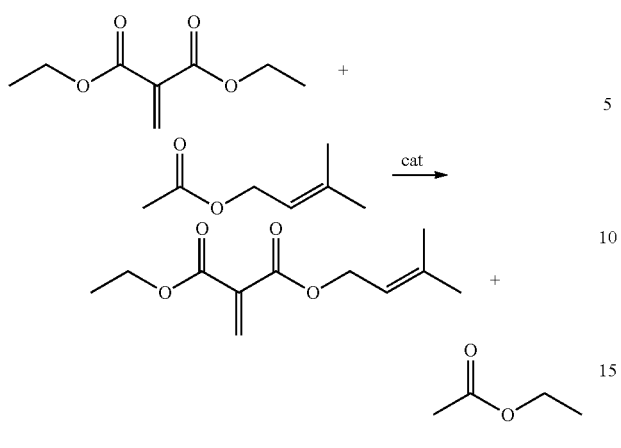

Examples 7 and 8—Preparation of EPMM and the Effects of Anionic Stabilizers

Two reactions are performed with pentanol as the reagent alcohol with either DBSA or MSA as the anionic stabilizer. To the round bottom flask set-up, a mixture of 30 g (1 equivalent) of DEMM, 5.120 g (0.33 equivalents) of pentanol, 2.163 (0.1 equivalent) of MeHQ, 2.844 g (0.05 equivalents) of DBSA or 0.167 g (0.01 equivalent) of MSA, and 0.261 (0.02 equivalents) of TFMSA is combined with agitation. Heat is applied to the reaction mixture and maintained at about 130° C. and mixed for 3 hours while applying reduced pressure at about 450 mmHg. Ethanol is collected as the reaction byproduct. GC-MS results are obtained and used to calculate conversion. EPMM has an elution time of about 7.93 minutes by GC-MS.

TABLE 1

| Acidic Stabilizer | Conversion to EPMM | DEMM + Ethanol Michael Byproduct | Total Reaction Polymeric Byproduct |
| --- | --- | --- | --- |
| MSA | 4.8% | 27.4% | 14.1% |
| DBSA | 74.4% | 3.9% | 2.2% |

The reaction is illustrated by the following equation:

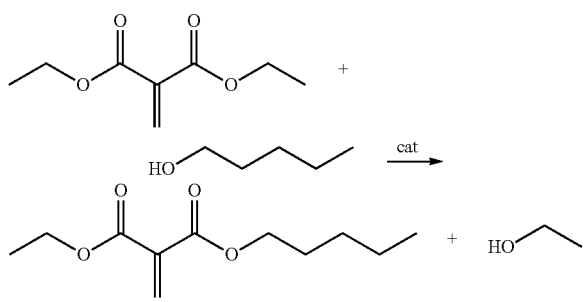

These examples illustrate how higher molecular weight acid compounds have the potential to improve the overall reaction by decreasing the amount of undesired Michael addition product (e.g., DEMM in the presence of a low molecular weight alcohol such as ethanol) as well as polymeric byproducts.

Example 9—Preparation of EAMM

To the round bottom flask set-up, a mixture of 30 g (1 equivalent) of DEMM, 5.815 g (0.33 equivalents) of allyl acetate, 4.362 (0.2 equivalents) of MeHQ, 2.844 g (0.05 equivalents) of DBSA, and 0.342 (0.02 equivalents) of sulfuric acid is combined with agitation. Heat is applied to the reaction mixture and maintained at about 80° C. and mixed for 6 hours while applying reduced pressure at about 450 mmHg. Ethyl acetate is collected as the reaction byproduct. GC-MS results were obtained and used to calculate conversion: 21.8% to EAMM under these conditions. This has an elution time of about 5.77 minutes by GC-MS. The reaction is illustrated by the following equation:

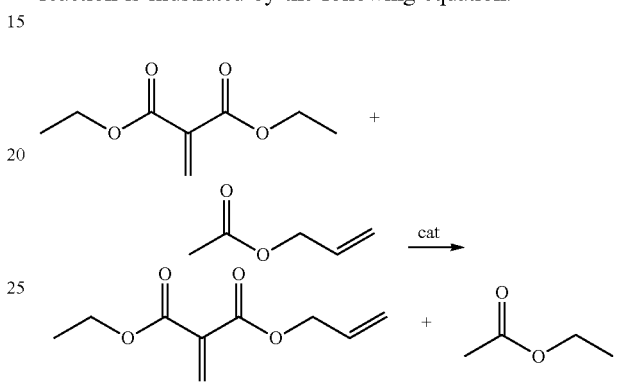

Example 10—Preparation of BEMM

To the round bottom flask set-up, a mixture of 30 g (1 equivalent) of DEMM, 8.722 g (0.33 equivalents) of benzyl acetate, 2.163 (0.1 equivalent) of MeHQ, 2.844 g (0.05 equivalents) of DBSA, and 0.342 (0.02 equivalents) of sulfuric acid is combined with agitation. Heat is applied to the reaction mixture and maintained at about 130° C. and mixed for 3 hours while applying reduced pressure at about 450 mmHg. Ethyl acetate is collected as the reaction byproduct. GC-MS results were obtained and used to calculate conversion: 39.6% to BEMM under these conditions. This has an elution time of about 10.27 minutes by GC-MS. The reaction is illustrated by the following equation:

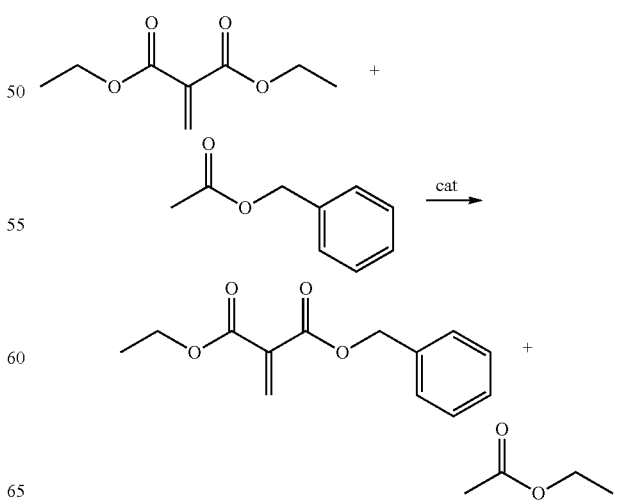

Example 11—Preparation of EBMM

To the round bottom flask set-up, a mixture of 30 g (1 equivalent) of DEMM, 5.932 g (0.33 equivalents) of butyl formate, 2.163 (0.1 equivalent) of MeHQ, 2.844 g (0.05 equivalents) of DBSA, and 0.342 (0.02 equivalents) of sulfuric acid is combined with agitation. Heat was applied to the reaction mixture and maintained at about 90° C. and mixed for 3 hours while applying reduced pressure at about 450 mmHg. Ethyl formate is collected as the reaction byproduct GC-MS results are obtained and used to calculate conversion: 46.9% to EBMM under these conditions. This has an elution time of about 6.97 minutes by GC-MS. The reaction is illustrated by the following equation:

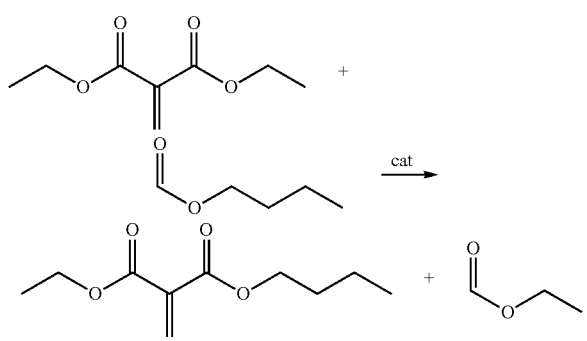

Example 12—Preparation EDiEGMM and Di-EDiEGMM

To the round bottom flask set-up, a mixture of 30 g (1 equivalent) of DEMM, 6.628 g (0.2 equivalents) of diethyleneglycol diacetate, 2.163 (0.1 equivalent) of MeHQ, 2.844 g (0.05 equivalents) of DBSA, and 0.342 (0.02 equivalents) of sulfuric acid is combined with agitation. Heat is applied to the reaction mixture and maintained at about 130° C. and mixed for 3 hours while applying reduced pressure at about 450 mmHg. Ethyl acetate is collected as the reaction byproduct. GC-MS results are obtained and used to calculate conversion: 22.8% to monosubstituted EDiEGMM with an elution time of about 10.93 minutes by GC-MS and 22.3% to Di-EDiEGMM with an elution time of about 14.21 minutes by GC-MS. The reaction is illustrated by the following equation:

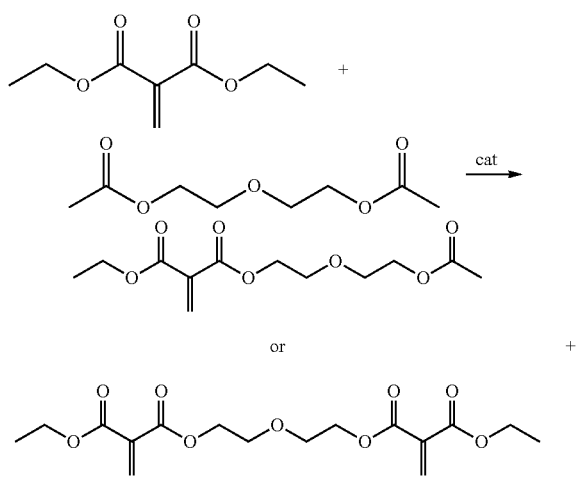

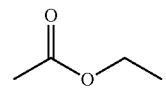

Example 13—Preparation of PEMM

To the round bottom flask set-up, a mixture of 20 g (1 equivalent) of DEMM, 6.09 g (0.33 equivalents) of 2-phenyl-1-propanol, and 0.99 g (0.025 equivalents) of BHT is charged. Reduced pressure of about 500 mmHg is maintained using a vacuum pump. The reaction mixture is then heated and maintained at about 130° C. Once the temperature reaches about 90° C., 0.27 g (0.025 equivalents) of sulfuric acid is added to the reaction mixture. The reaction is then stirred for 2 hours. Ethanol is collected as the reaction byproduct. Yield is calculated for this reaction and based on amount of product isolated from reaction mixture by distillation: 50.0% to PEMM under these conditions. This has an elution time of about 11.3 minutes by GC-MS. The reaction is illustrated by the following equation:

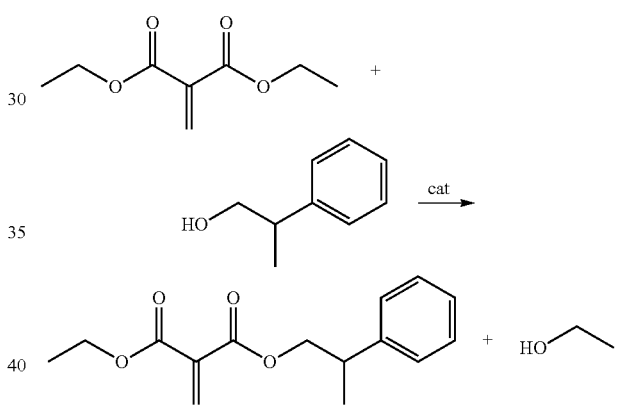

Example 14—Preparation of FEMM

To the round bottom flask set-up, a mixture of 20 g (1 equivalent) of DEMM, 6.09 g (0.33 equivalents) of fenchol, and 0.99 g (0.036 equivalents) of BHT is charged. Reduced pressure of about 500 mmHg was maintained using a vacuum pump. The reaction mixture is then heated and maintained at about 130° C. Once the temperature reaches about 90° C., 0.27 g (0.025 equivalents) of sulfuric acid is added to the reaction mixture. The reaction is then stirred for 2 hours. Ethanol is collected as the reaction byproduct. GC-MS results were obtained and used to calculate conversion: 29.5% to FEMM under these conditions. This has an elution time of about 10.55 minutes by GC-MS. The reaction is illustrated by the following equation:

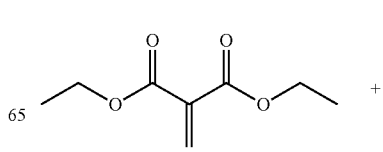

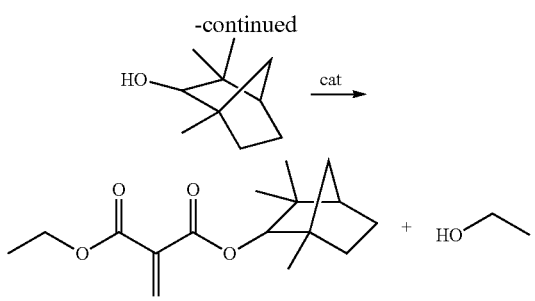

Example 15—Preparation of MEMM

To the round bottom flask set-up, a mixture of 20 g (1 equivalent) of DEMM, 6.09 g (0.3 equivalents) of menthol and 0.67 g (0.025 equivalents) of BHT is charged. Reduced pressure of about 500 mmHg is maintained using a vacuum pump. The reaction mixture is then heated and maintained at about 130° C. Once the temperature reaches 90° C., 0.27 g (0.025 equivalents) of sulfuric acid was added to the reaction mixture. The reaction is then stirred for 2 hours. Ethanol is collected as the reaction byproduct. GC-MS results were obtained and used to calculate conversion: 69.4% to MEMM under these conditions. This has an elution time of about 11.0 minutes by GC-MS. The reaction is illustrated by the following equation:

Example 16 Preparation of EPMM and Di-EHMM Using a Number of Catalysts

The pentanol and pentyl acetate reactions are performed using these representative reaction conditions: the reaction temperature maintained at about 115-130° C. and about 300-500 mmHg of reduced pressure was used. The point at which optimum conversion is seen is reported along with the reaction time below in Table 2. Total reaction time is limited to 4 hours for these reactions. In these examples, the monomer to alcohol or acetate ratio is about 3:1. The homogeneous catalysts are added at about 0.01 equivalent to DEMM monomer. The heterogeneous catalysts are added at about 5 weight percent of the total monomer. The remaining materials are incorporated at similar equivalents for each reaction: DBSA (0.05) and MeHQ or BHT (0.1). The results below show the percent conversion via GC-MS to the targeted product, which in this case is EPMM having an elution time of about 7.93 minutes by GC-MS. The results are compiled in Table 2. The reaction is illustrated by the following equation:

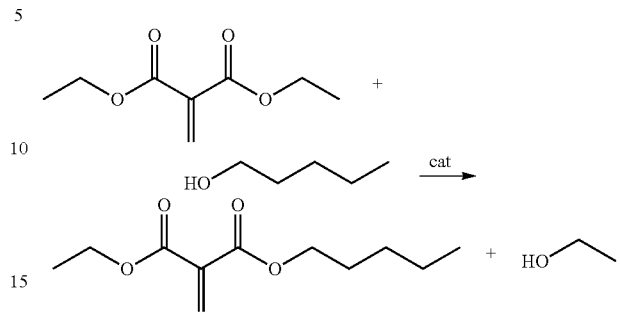

The reactions with hexane diol are performed at about 130° C. and 300-500 mmHg of reduced pressure for a period of time up to 3 hours using various acid catalysts. For reactions using TMFSA, Nafion, and ethyl triflate, the formation of polymeric side products is problematic and prevalent for this reaction reagent. In these cases catalyst loading is 0.01 equivalent to DEMM. DBSA is used as a stabilizer at 0.05 equivalent to DEMM. For all other liquid catalysts listed, 0.5 weight percent of total reactant mixture is utilized. DBSA was not added as an anionic stabilizer. For Amberlyst, 5 weight percent of the total reaction mixture is used along with BHT in amounts between 0.025 to 0.1 mole equivalents to DEMM monomer. The ratio of DEMM to 1,6 hexanediol in each of these reactions is about 5:1. The desired product is Di-EHMM which has an elution time of about 15.45 minutes by GC-MS. The results are compiled in Table 2. Monosubstituted EHMM (i.e., with an unreacted primary hydroxyl group) has also been observed under certain reaction conditions. This has an elution time of about 11.05 minutes by GC-MS. The reaction is illustrated by the following equation:

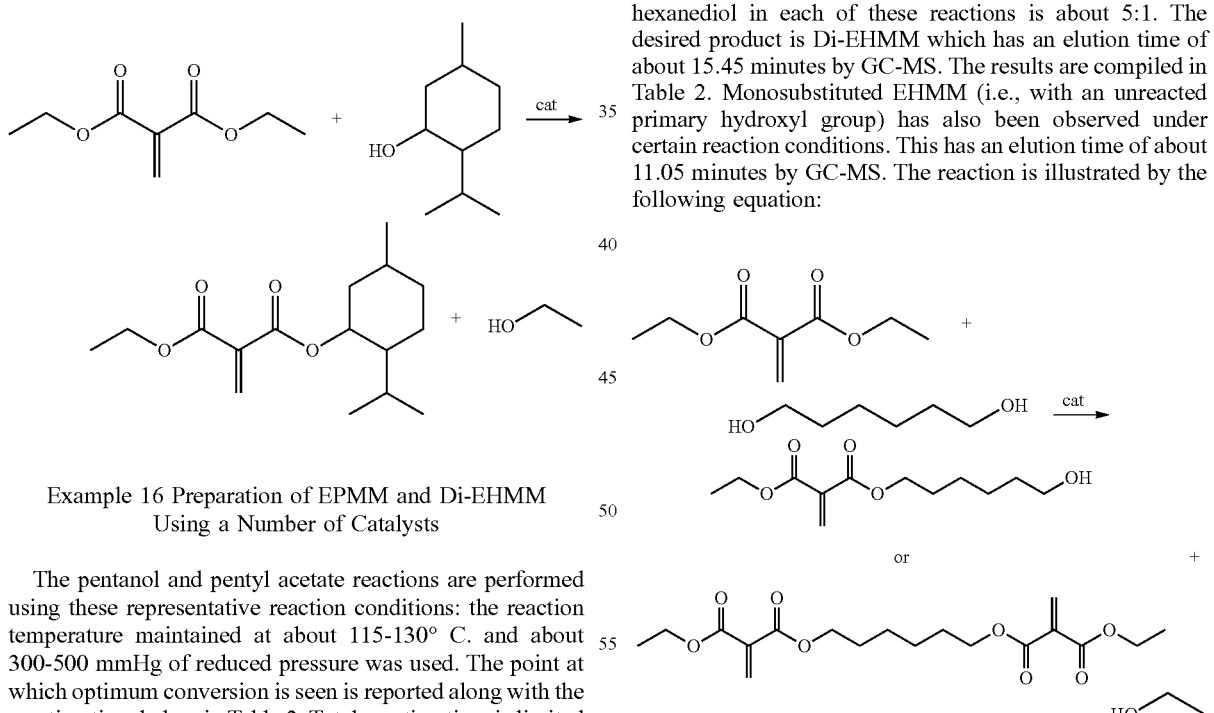

TABLE 2

| Catalyst | Pentyl acetate Conversion/Time | Pentanol Conversion/Time | Hexane Diol Conversion/Time |
|---|---|---|---|
| Phosphoric acid pKa: 2.148 | 35.4%/3 h | 64.7%/3 h | 6.8%/3 h |

TABLE 2-continued

| Catalyst | Pentyl acetate Conversion/Time | Pentanol Conversion/Time | Hexane Diol Conversion/Time |
|---|---|---|---|
| Tetrafluoroboric acid diethyl ether complex | 64.8%/3 h | 58.4%/1 h | 2.5%/3 h |
| Methanesulfonic acid | 0.1% 3 h | 84.9% 3 h | 9.4% 3 h |
| Sulfuric acid | 88.3% 4 h | 74.4% 1 h | 51.3% 2 h |
| Amberlyst 15 hydrogen form (Heterogeneous sulfuric acid) | 40.3% 3 h | 35.0% 3 h | 0% 3 h |
| Fluorosulfonic acid | 82.3% 3 h | 62.4% 3 h | 78.6% 3 h |
| TFMSA | 52.3% 3 h | 25.7% 3 h | 32.4% 30 min |
| Nafion NR50 (Heterogeneous TFMSA) | 18.9% 3 h | 11.6% 3 h | 88.9% 2 h |
| Ethyl triflate | 45.0% 4 h | 31.8% 4 h | 40.2% 2 h |
| Dibutyl sulfate | 47.4% 3 h | 64.7% 2 h | 5.1% 3 h |

The results show choice of a catalyst system greatly affects the final yield of the desired product in proportion to the side reactions caused by Michael addition across the methylene double bond and polymerization. Weaker acids transesterify appreciable amounts of the starting reactants to give desired products where monosubstitution is desired (ethyl pentyl methylene malonate). Stronger acids are desired to obtain appreciable yields of transesterified difunctional products.

Example 17 Preparation of Various 1,1-Disubstituted Alkenes Using Sulfuric Acid as the Reaction Catalyst The examples are performed substantially as described in Example 16. The first three runs are the sulfuric acid catalyzed reactions in Example 17. The results are compiled in Table 3.

TABLE 3

| Alcohol/Second ester | Conversion % | Time hours |
|---|---|---|
| Pentyl acetate | 88.3 | 4 |
| Pentanol | 74.4 | 2 |
| Hexane Diol | 51.3 | 2 |
| 2-phenyl-1-propanol | 50.0 | 2 |
| Fenchol | 29.5 | 2 |
| Menthol | 69.4 | 2 |

Parts by weight as used herein refers to 100 parts by weight of the composition specifically referred to. Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32, etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value, and the highest value enumerated are to be considered to be expressly stated in this application in a similar manner. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

The invention claimed is:

1. A method comprising: contacting a first ester compound having one or more ester groups with hydrocarbyl moieties as part of each of the ester groups and a functional group which may undergo undesired side reactions under transesterification reaction conditions, with one or more alcohols having a hydrocarbon backbone and one or more hydroxyl groups or one or more second ester compounds having one or more ester groups with hydrocarbyl moieties different from the hydrocarbyl moieties on the first ester compounds, in the presence of one or more acids having a pKa in a polar aprotic solvent of about −5 to less than 8 or esters of the acid under conditions that at least one of the hydrocarbyl moieties on the first ester compound is replaced by the alcohol hydrocarbon backbone or hydrocarbyl moieties from the second ester compounds; wherein the catalyst is present in an amount of 0.001 molar equivalents to 0.1 molar equivalents based on the molar equivalents of the first ester compound and the reactants are contacted at a temperature of about 80° C. to about 160° C. wherein the functional group which may undergo undesired side reactions under transesterification reaction conditions is an unsaturated group and the unsaturated group is in the proximity of one or more electron withdrawing groups such that the electrophilicity or electron withdrawing characteristics of the unsaturated group are increased.

2. A method according to claim 1 wherein the hydrocarbyl moiety removed from the first ester compound forms a second alcohol or a third ester compound as a byproduct and the second alcohol or third ester compound formed is removed.

3. A composition comprising one or more first 1,1-diester-substituted alkenes and one or more compounds containing two or more core units of 1,1-diester-substituted alkenes linked by at least one of the oxygen atoms of the ester groups which are bonded to the hydrocarbon backbone of one or more alcohols having two or more hydroxyl groups or the hydrocarbon backbone of one or more second ester compounds having two or more ester groups wherein the concentration of and one or more compounds containing two or more core units of 1,1-diester-substituted alkenes is greater than 5 percent by weight; wherein the core units correspond to the formula

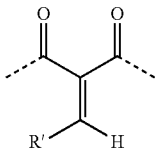

wherein R' is separately in each occurrence hydrocarbyl or hydrogen.

4. A composition according to claim 3 wherein the first 1,1-diester-substituted alkenes correspond to at least one of the formulas:

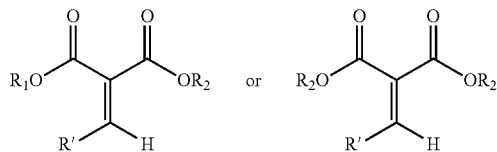

and the one or more compounds containing two or more core units of 1,1-diester-substituted alkenes correspond to at least one of the formulas:

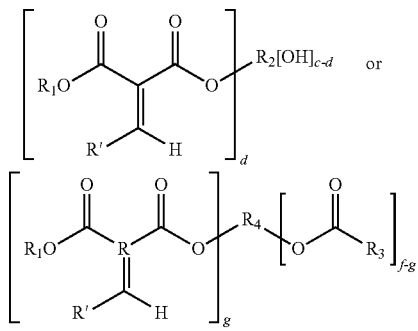

wherein:
$R_1$, $R_2$, and $R_3$ are separately in each occurrence hydrocarbyl groups;
$R_4$ is separately in each occurrence an f-valent hydrocarbyl group;
R' is separately in each occurrence hydrocarbyl or hydrogen;
c is separately in each occurrence an integer of 2 or more;
d is separately in each occurrence an integer of 1 or more and is less than c;
f is separately in each occurrence an integer of 2 or greater; and
g is an integer of 1 or greater, with the proviso that g is less than f.

5. A composition comprising one or more first 1,1-diester-substituted alkenes linked by at least one of the oxygen atoms of the ester groups which are bonded to the hydrocarbon backbone of one or more second ester compounds wherein the hydrocarbon backbone of the one or more second ester compounds is bonded to one or more ester groups.

6. A composition according to claim 5 wherein the hydrocarbon back bone is bonded to an acrylate, acetate or formate group.

7. A composition according to claim 5 illustrated by the formula:

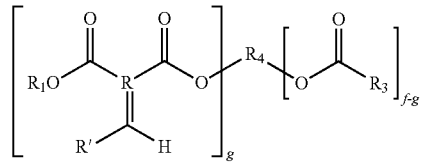

wherein:
$R_1$, and $R_3$ are separately in each occurrence hydrocarbyl groups;
R4 is separately in each occurrence an f-valent hydrocarbyl group;
R' is separately in each occurrence hydrocarbyl or hydrogen;
f is separately in each occurrence an integer of 2 or greater; and
g is an integer of 1 or greater with the proviso that f is greater than g.

8. A composition according to claim 7 wherein R' is hydrogen and $R_3$ is hydrogen or methyl.

9. A composition according to claim 3 which is illustrated by the formula:

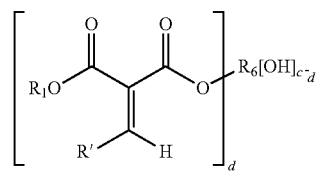

wherein:
$R_1$ is separately in each occurrence hydrocarbyl groups;
R' is separately in each occurrence hydrocarbyl or hydrogen;
$R_6$ is the residue of an alkyl acrylate;
c is separately in each occurrence an integer of 3 or more;
d is separately in each occurrence an integer of 2 or more and is less than c.

10. A method according to claim 1 wherein the catalyst is trifluoromethanesulfonic acid, sulfated tin oxide, triflated tin oxide, sulfated zirconia, triflated zirconia, triflated HZSM-5 or fluorosulfonic acid.

11. A method according to claim 1 wherein the catalyst is trifluoromethanesulfonic acid or fluorosulfonic acid.

12. A method according to claim 1 the reactants are reacted at a temperature of about 80° C. to about 140° C.

13. A method according to claim 1 the reactants are reacted at a temperature of about 80° C. to about 130° C.

14. A method according to claim 1 wherein the reactants are reacted for about 1 to about 4 hours.

15. A method according to claim 1 wherein the reactants are contacted in the present of a polar aprotic solvent having a boiling point at least 15° C. above the temperature at which the reactants are contacted.

16. A method according to claim 1 wherein the reactants are reacted with agitation.

* * * * *